(12) United States Patent
Calef et al.

(10) Patent No.: US 11,857,153 B2
(45) Date of Patent: Jan. 2, 2024

(54) SYSTEMS AND METHODS FOR MULTI-MODAL SENSING OF DEPTH IN VISION SYSTEMS FOR AUTOMATED SURGICAL ROBOTS

(71) Applicant: Activ Surgical, Inc., Boston, MA (US)

(72) Inventors: Thomas J. Calef, Boston, MA (US); Tina P. Chen, Boston, MA (US); Emanuel Demaio, Boston, MA (US); Tony Chen, Boston, MA (US); Vasiliy Evgenyevich Buharin, Boston, MA (US); Michael G. Ruehlman, Boston, MA (US)

(73) Assignee: Activ Surgical, Inc., Boston, MA (US)

(*) Notice: Subject to any disclaimer, the term of this patent is extended or adjusted under 35 U.S.C. 154(b) by 85 days.

(21) Appl. No.: 17/512,543

(22) Filed: Oct. 27, 2021

(65) Prior Publication Data

US 2022/0117689 A1 Apr. 21, 2022

Related U.S. Application Data

(63) Continuation of application No. 17/150,701, filed on Jan. 15, 2021, now Pat. No. 11,179,218, which is a
(Continued)

(51) Int. Cl.
*G06T 7/521* (2017.01)
*A61B 1/00* (2006.01)
(Continued)

(52) U.S. Cl.
CPC .......... *A61B 1/000094* (2022.02); *A61B 1/00* (2013.01); *A61B 1/000095* (2022.02);
(Continued)

(58) Field of Classification Search
CPC ..................................................... G06T 7/521
See application file for complete search history.

(56) References Cited

U.S. PATENT DOCUMENTS

| 6,088,105 A | 7/2000 | Link |
| 6,373,963 B1 | 4/2002 | Demers et al. |

(Continued)

FOREIGN PATENT DOCUMENTS

| CN | 102385237 A | 3/2012 |
| JP | 2013544449 A | 12/2013 |

(Continued)

OTHER PUBLICATIONS

Extended European Search Report for European Patent Application No. 19838270.7 dated Mar. 28, 2022.
(Continued)

*Primary Examiner* — Oneal R Mistry
(74) *Attorney, Agent, or Firm* — Wilson Sonsini Goodrich & Rosati

(57) ABSTRACT

Systems and methods for multi-modal sensing of three-dimensional position information of the surface of an object are disclosed. In particular, multiple visualization modalities are each used to collect distinctive positional information of a surface of an object. Each of the computed positional information is combined using weighting factors to compute a final, weighted three-dimensional position. In various embodiments, a first depth may be recorded using fiducial markers, a second depth may be recorded using a structured light pattern, and a third depth may be recorded using a light-field camera. Weighting factors may be applied to each of the recorded depths and a final, weighted depth may be computed.

21 Claims, 25 Drawing Sheets

Related U.S. Application Data continuation of application No. PCT/US2019/042647, filed on Jul. 19, 2019.

(60) Provisional application No. 62/700,700, filed on Jul. 19, 2018.

(51) Int. Cl.
*A61B 90/00* (2016.01)
*G06T 7/557* (2017.01)
*G06T 7/593* (2017.01)
*H04N 13/239* (2018.01)

(52) U.S. Cl.
CPC .......... *A61B 1/00193* (2013.01); *A61B 90/06* (2016.02); *G06T 7/521* (2017.01); *G06T 7/557* (2017.01); *G06T 7/593* (2017.01); *H04N 13/239* (2018.05); *A61B 2090/062* (2016.02); *A61B 2090/363* (2016.02); *A61B 2090/371* (2016.02); *A61B 2090/3933* (2016.02); *A61B 2090/3937* (2016.02)

(56) References Cited

U.S. PATENT DOCUMENTS

| | | |
|---|---|---|
| 6,491,702 B2 | 12/2002 | Heilbrun et al. |
| 6,503,195 B1 | 1/2003 | Keller et al. |
| 6,542,249 B1 | 4/2003 | Kofman et al. |
| 6,549,288 B1 | 4/2003 | Migdal et al. |
| 6,563,105 B2 | 5/2003 | Seibel et al. |
| 6,564,086 B2 | 5/2003 | Marchitto et al. |
| 6,613,041 B1 | 9/2003 | Schrunder |
| 6,697,164 B1 | 2/2004 | Babayoff et al. |
| 6,800,057 B2 | 10/2004 | Tsujita et al. |
| 6,850,872 B1 | 2/2005 | Marschner et al. |
| 6,873,867 B2 | 3/2005 | Vilsmeier |
| 6,885,464 B1 | 4/2005 | Pfeiffer et al. |
| RE38,800 E | 9/2005 | Barbour |
| 6,965,690 B2 | 11/2005 | Matsumoto |
| 6,977,732 B2 | 12/2005 | Chen et al. |
| 6,987,531 B2 | 1/2006 | Kamon |
| 7,006,236 B2 | 2/2006 | Tomasi et al. |
| 7,068,825 B2 | 6/2006 | Rubbert et al. |
| 7,092,107 B2 | 8/2006 | Babayoff et al. |
| 7,099,732 B2 | 8/2006 | Geng |
| 7,124,066 B2 | 10/2006 | Marschner et al. |
| 7,152,024 B2 | 12/2006 | Marschner et al. |
| 7,184,150 B2 | 2/2007 | Quadling et al. |
| 7,200,262 B2 | 4/2007 | Sawada |
| 7,224,384 B1 | 5/2007 | Iddan et al. |
| 7,230,725 B2 | 6/2007 | Babayoff et al. |
| 7,242,997 B2 | 7/2007 | Geng |
| 7,305,110 B2 | 12/2007 | Rubbert et al. |
| 7,313,264 B2 | 12/2007 | Crampton |
| 7,319,529 B2 | 1/2008 | Babayoff |
| 7,363,201 B2 | 4/2008 | Marschner et al. |
| 7,385,708 B2 | 6/2008 | Ackerman et al. |
| 7,433,807 B2 | 10/2008 | Marschner et al. |
| 7,435,217 B2 | 10/2008 | Wiklof |
| 7,450,783 B2 | 11/2008 | Talapov et al. |
| 7,477,402 B2 | 1/2009 | Babayoff et al. |
| 7,489,408 B2 | 2/2009 | Harding et al. |
| 7,491,956 B2 | 2/2009 | Knoche et al. |
| 7,492,927 B2 | 2/2009 | Marschner et al. |
| 7,511,829 B2 | 3/2009 | Babayoff |
| 7,522,764 B2 | 4/2009 | Schwotzer |
| 7,577,299 B2 | 8/2009 | Kawamata et al. |
| 7,620,209 B2 | 11/2009 | Stevick et al. |
| 7,630,089 B2 | 12/2009 | Babayoff et al. |
| 7,704,206 B2 | 4/2010 | Suzuki et al. |
| 7,724,378 B2 | 5/2010 | Babayoff |
| 7,724,932 B2 | 5/2010 | Ernst et al. |
| 7,751,871 B2 | 7/2010 | Rubbert |
| 7,763,841 B1 | 7/2010 | McEldowney |
| 7,794,388 B2 | 9/2010 | Draxinger et al. |
| 7,821,649 B2 | 10/2010 | Bendall et al. |
| 7,854,700 B2 | 12/2010 | Orihara |
| 7,898,651 B2 | 3/2011 | Hu et al. |
| 7,944,569 B2 | 5/2011 | Babayoff et al. |
| 7,951,073 B2 | 5/2011 | Freed |
| 7,961,912 B2 | 6/2011 | Stevick et al. |
| 7,967,743 B2 | 6/2011 | Ishihara |
| 7,990,548 B2 | 8/2011 | Babayoff et al. |
| 7,995,798 B2 | 8/2011 | Krupnik et al. |
| 8,027,710 B1 | 9/2011 | Dannan |
| 8,038,609 B2 | 10/2011 | Kohno et al. |
| 8,084,753 B2 | 12/2011 | Joshi et al. |
| 8,264,536 B2 | 9/2012 | McEldowney |
| 8,279,418 B2 | 10/2012 | Yee et al. |
| 8,280,152 B2 | 10/2012 | Thiel et al. |
| 8,310,683 B2 | 11/2012 | Babayoff et al. |
| 8,320,621 B2 | 11/2012 | McEldowney |
| 8,326,020 B2 | 12/2012 | Lee et al. |
| 8,330,804 B2 | 12/2012 | Lutian et al. |
| 8,400,494 B2 | 3/2013 | Zalevsky et al. |
| 8,406,859 B2 | 3/2013 | Zuzak et al. |
| 8,471,897 B2 | 6/2013 | Rodriguez Ramos et al. |
| 8,517,928 B2 | 8/2013 | Orihara |
| 8,553,939 B2 | 10/2013 | Craig et al. |
| 8,558,873 B2 | 10/2013 | McEldowney |
| 8,593,507 B2 | 11/2013 | Yahav |
| 8,610,665 B2 | 12/2013 | Craig et al. |
| 8,649,024 B2 | 2/2014 | Colonna De Lega |
| 8,659,765 B2 | 2/2014 | Ando |
| 8,723,118 B2 | 5/2014 | McEldowney et al. |
| 8,723,923 B2 | 5/2014 | Bloom et al. |
| 8,744,167 B2 | 6/2014 | Kang et al. |
| 8,755,053 B2 | 6/2014 | Fright et al. |
| 8,792,098 B2 | 7/2014 | Dewald et al. |
| 8,803,952 B2 | 8/2014 | Katz et al. |
| 8,823,790 B2 | 9/2014 | Dunn et al. |
| 8,872,824 B1 | 10/2014 | Phillips et al. |
| 8,891,087 B2 | 11/2014 | Zuzak et al. |
| 8,896,594 B2 | 11/2014 | Xiong et al. |
| 8,974,378 B2 | 3/2015 | Imaizumi et al. |
| 9,001,190 B2 | 4/2015 | Olivier, III et al. |
| 9,057,784 B2 | 6/2015 | Hudman |
| 9,068,824 B2 | 6/2015 | Findeisen et al. |
| 9,070,194 B2 | 6/2015 | Lee et al. |
| 9,072,445 B2 | 7/2015 | Berguer et al. |
| 9,074,868 B2 | 7/2015 | Bendall et al. |
| 9,089,277 B2 | 7/2015 | Babayoff et al. |
| 9,119,552 B2 | 9/2015 | Baumann et al. |
| 9,135,502 B2 | 9/2015 | Haker et al. |
| 9,142,025 B2 | 9/2015 | Park et al. |
| 9,147,253 B2 | 9/2015 | Yee et al. |
| 9,149,348 B2 | 10/2015 | Wu et al. |
| 9,157,728 B2 | 10/2015 | Ogawa |
| 9,157,733 B2 | 10/2015 | Dillon et al. |
| 9,198,578 B2 | 12/2015 | Zuzak et al. |
| 9,204,952 B2 | 12/2015 | Lampalzer |
| 9,220,570 B2 | 12/2015 | Kim et al. |
| 9,226,645 B2 | 1/2016 | Ntziachristos |
| 9,226,673 B2 | 1/2016 | Ferguson, Jr. et al. |
| 9,247,865 B2 | 2/2016 | Igarashi et al. |
| 9,254,076 B2 | 2/2016 | McDowall |
| 9,254,078 B2 | 2/2016 | McDowall |
| 9,254,103 B2 | 2/2016 | Krishnaswamy et al. |
| 9,261,356 B2 | 2/2016 | Lampert et al. |
| 9,261,358 B2 | 2/2016 | Atiya et al. |
| 9,271,658 B2 | 3/2016 | Ferguson, Jr. et al. |
| 9,274,047 B2 | 3/2016 | Velten et al. |
| 9,282,926 B2 | 3/2016 | Schwotzer et al. |
| 9,294,758 B2 | 3/2016 | Xiong et al. |
| 9,297,889 B2 | 3/2016 | Hudman et al. |
| 9,304,603 B2 | 4/2016 | Miller |
| 9,330,464 B1 | 5/2016 | Ackerman et al. |
| 9,345,389 B2 | 5/2016 | Nie et al. |
| 9,345,392 B2 | 5/2016 | Saito |
| 9,345,397 B2 | 5/2016 | Taylor et al. |
| 9,351,643 B2 | 5/2016 | Sharonov |
| 9,364,300 B2 | 6/2016 | Tchouprakov et al. |
| 9,375,844 B2 | 6/2016 | Itkowitz et al. |
| 9,377,295 B2 | 6/2016 | Fright et al. |

(56) References Cited

U.S. PATENT DOCUMENTS

| | | |
|---|---|---|
| 9,380,224 B2 | 6/2016 | Keskin et al. |
| 9,389,068 B2 | 7/2016 | Ri |
| 9,404,741 B2 | 8/2016 | Schick |
| 9,432,593 B2 | 8/2016 | Yang et al. |
| 9,439,568 B2 | 9/2016 | Atiya et al. |
| 9,443,310 B2 | 9/2016 | Hudman et al. |
| 9,444,981 B2 | 9/2016 | Bellis et al. |
| 9,451,872 B2 | 9/2016 | Yokota |
| 9,462,253 B2 | 10/2016 | Hudman et al. |
| 9,471,864 B2 | 10/2016 | Zatloukal et al. |
| 9,491,441 B2 | 11/2016 | Sarmast et al. |
| 9,494,418 B2 | 11/2016 | Schmidt |
| 9,506,749 B2 | 11/2016 | Bellis et al. |
| 9,513,113 B2 | 12/2016 | Yang et al. |
| 9,513,768 B2 | 12/2016 | Zhao et al. |
| 9,545,220 B2 | 1/2017 | Sidlesky |
| 9,557,574 B2 | 1/2017 | McEldowney |
| 9,581,802 B2 | 2/2017 | Yokota |
| 9,615,901 B2 | 4/2017 | Babayoff et al. |
| 9,622,644 B2 | 4/2017 | Yokota |
| 9,622,662 B2 | 4/2017 | Zuzak et al. |
| 9,638,801 B2 | 5/2017 | Boufounos et al. |
| 9,674,436 B2 | 6/2017 | Crane et al. |
| 9,675,429 B2 | 6/2017 | Lampert et al. |
| 9,690,984 B2 | 6/2017 | Butler et al. |
| 9,696,427 B2 | 7/2017 | Wilson et al. |
| 9,720,506 B2 | 8/2017 | Kim et al. |
| 9,729,860 B2 | 8/2017 | Cohen et al. |
| 9,737,239 B2 | 8/2017 | Kimmel |
| 9,739,594 B2 | 8/2017 | Koerner et al. |
| 9,746,318 B2 | 8/2017 | Sugano |
| 9,752,867 B2 | 9/2017 | Atiya et al. |
| 9,782,056 B2 | 10/2017 | McDowall |
| 9,788,903 B2 | 10/2017 | Kim et al. |
| 9,799,117 B2 | 10/2017 | Chen et al. |
| 9,817,159 B2 | 11/2017 | Hudman |
| 9,833,145 B2 | 12/2017 | Jeong et al. |
| 9,841,496 B2 | 12/2017 | Hudman |
| 9,844,427 B2 | 12/2017 | Atiya et al. |
| 9,901,409 B2 | 2/2018 | Yang et al. |
| 9,918,640 B2 | 3/2018 | Ntziachristos et al. |
| 9,922,249 B2 | 3/2018 | Kang et al. |
| 9,939,258 B2 | 4/2018 | Lampert et al. |
| 9,943,271 B2 | 4/2018 | Dirauf et al. |
| 9,947,099 B2 | 4/2018 | Bleyer et al. |
| 9,953,428 B2 | 4/2018 | Gren et al. |
| 9,955,140 B2 | 4/2018 | Rhemann et al. |
| 9,955,861 B2 | 5/2018 | Gao et al. |
| 9,958,585 B2 | 5/2018 | Powell et al. |
| 9,958,758 B2 | 5/2018 | Hudman |
| 9,962,244 B2 | 5/2018 | Esbech et al. |
| 9,970,753 B2 | 5/2018 | Han et al. |
| 10,011,014 B2 | 7/2018 | Divoky et al. |
| 10,018,464 B2 | 7/2018 | Boles et al. |
| 10,024,968 B2 | 7/2018 | Hudman et al. |
| 10,039,439 B2 | 8/2018 | Aoyama |
| 10,045,882 B2 | 8/2018 | Balicki et al. |
| 10,055,856 B2 | 8/2018 | Sabater et al. |
| 10,058,256 B2 | 8/2018 | Chen et al. |
| 10,066,997 B2 | 9/2018 | Korner et al. |
| 10,089,737 B2 | 10/2018 | Krieger et al. |
| 10,244,991 B2 | 4/2019 | Shademan et al. |
| 10,390,718 B2 | 8/2019 | Chen et al. |
| 10,398,519 B2 | 9/2019 | Kim et al. |
| 10,675,040 B2 | 6/2020 | Kim et al. |
| 10,722,173 B2 | 7/2020 | Chen et al. |
| 10,792,492 B2 | 10/2020 | Chen et al. |
| 10,948,350 B2 | 3/2021 | Ferguson, Jr. et al. |
| 11,135,028 B2 | 10/2021 | Kim et al. |
| 11,179,218 B2 | 11/2021 | Calef et al. |
| 11,278,220 B2 | 3/2022 | Tucker et al. |
| 2003/0195623 A1 | 10/2003 | Marchitto et al. |
| 2004/0114033 A1 | 6/2004 | Eian et al. |
| 2004/0239673 A1 | 12/2004 | Schmidt |
| 2005/0096515 A1 | 5/2005 | Geng |
| 2005/0116950 A1 | 6/2005 | Hoppe |
| 2005/0253849 A1 | 11/2005 | Reddy et al. |
| 2007/0115484 A1 | 5/2007 | Huang et al. |
| 2007/0146719 A1 | 6/2007 | Wedel |
| 2007/0165243 A1 | 7/2007 | Kang et al. |
| 2007/0280423 A1 | 12/2007 | Schmidt |
| 2008/0107305 A1 | 5/2008 | Vanderkooy et al. |
| 2008/0123910 A1 | 5/2008 | Zhu |
| 2008/0266391 A1 | 10/2008 | Lee et al. |
| 2008/0291463 A1* | 11/2008 | Milner ............... G01B 9/02069 356/491 |
| 2009/0221874 A1 | 9/2009 | Vinther et al. |
| 2009/0244260 A1 | 10/2009 | Takahashi et al. |
| 2010/0113921 A1 | 5/2010 | Fear et al. |
| 2010/0265557 A1 | 10/2010 | Sallander |
| 2011/0015518 A1 | 1/2011 | Schmidt et al. |
| 2011/0043609 A1 | 2/2011 | Choi et al. |
| 2011/0057930 A1 | 3/2011 | Keller et al. |
| 2011/0080471 A1 | 4/2011 | Song et al. |
| 2011/0123098 A1 | 5/2011 | Ernst et al. |
| 2012/0056982 A1 | 3/2012 | Katz et al. |
| 2012/0075432 A1 | 3/2012 | Bilbrey et al. |
| 2012/0095354 A1 | 4/2012 | Dunn et al. |
| 2012/0165681 A1 | 6/2012 | Keller |
| 2012/0176481 A1 | 7/2012 | Lukk et al. |
| 2012/0206587 A1 | 8/2012 | Oz et al. |
| 2012/0268491 A1 | 10/2012 | Sugden et al. |
| 2012/0294498 A1 | 11/2012 | Popovic |
| 2012/0310098 A1 | 12/2012 | Popovic |
| 2013/0023732 A1 | 1/2013 | Kim et al. |
| 2013/0129194 A1 | 5/2013 | Gusis et al. |
| 2013/0253313 A1 | 9/2013 | Kang et al. |
| 2013/0274596 A1 | 10/2013 | Azizian et al. |
| 2013/0296712 A1 | 11/2013 | Durvasula |
| 2014/0031665 A1 | 1/2014 | Pinto et al. |
| 2014/0052005 A1 | 2/2014 | Yokota |
| 2014/0071257 A1 | 3/2014 | Yokota |
| 2014/0092281 A1 | 4/2014 | Nisenzon et al. |
| 2014/0169629 A1 | 6/2014 | Beaty et al. |
| 2014/0177943 A1 | 6/2014 | Cho et al. |
| 2014/0184769 A1 | 7/2014 | Ishihara et al. |
| 2014/0194747 A1 | 7/2014 | Kruglick et al. |
| 2015/0062370 A1 | 3/2015 | Shroff et al. |
| 2015/0086956 A1 | 3/2015 | Savitsky et al. |
| 2015/0164329 A1 | 6/2015 | Schmidt et al. |
| 2015/0213646 A1 | 7/2015 | Ma et al. |
| 2015/0238276 A1 | 8/2015 | Atarot et al. |
| 2015/0377613 A1 | 12/2015 | Small et al. |
| 2016/0128553 A1 | 5/2016 | Geng |
| 2016/0139039 A1 | 5/2016 | Ikehara et al. |
| 2016/0239978 A1 | 8/2016 | Cole et al. |
| 2016/0260206 A1 | 9/2016 | Jung et al. |
| 2016/0262615 A1 | 9/2016 | Jung et al. |
| 2016/0278678 A1 | 9/2016 | Valdes et al. |
| 2016/0300348 A1 | 10/2016 | Nadeau et al. |
| 2016/0307325 A1 | 10/2016 | Wang et al. |
| 2016/0307326 A1 | 10/2016 | Wang |
| 2016/0309068 A1 | 10/2016 | Nadeau et al. |
| 2016/0335472 A1 | 11/2016 | Lee et al. |
| 2017/0014030 A1 | 1/2017 | Rentschler et al. |
| 2017/0020393 A1 | 1/2017 | Rentschler et al. |
| 2017/0026633 A1 | 1/2017 | Riza |
| 2017/0030710 A1 | 2/2017 | Rentschler et al. |
| 2017/0032531 A1 | 2/2017 | Nagata et al. |
| 2017/0059305 A1 | 3/2017 | Nonn et al. |
| 2017/0079724 A1 | 3/2017 | Yang et al. |
| 2017/0100024 A1 | 4/2017 | Shahmoon et al. |
| 2017/0143237 A1 | 5/2017 | Yokota |
| 2017/0164836 A1 | 6/2017 | Krishnaswamy et al. |
| 2017/0172382 A1 | 6/2017 | Nir et al. |
| 2017/0172384 A1 | 6/2017 | Yokota |
| 2017/0209031 A1 | 7/2017 | Nakamura et al. |
| 2017/0227942 A1 | 8/2017 | Thomson et al. |
| 2017/0228879 A1 | 8/2017 | Sato |
| 2017/0251900 A1 | 9/2017 | Hansen et al. |
| 2017/0258526 A1 | 9/2017 | Lang |
| 2017/0280970 A1 | 10/2017 | Sartor et al. |
| 2017/0328704 A1 | 11/2017 | Atiya et al. |
| 2017/0337703 A1 | 11/2017 | Wu et al. |

(56) References Cited

U.S. PATENT DOCUMENTS

| | | |
|---|---|---|
| 2017/0347043 A1 | 11/2017 | Rephaeli et al. |
| 2017/0366773 A1 | 12/2017 | Kiraly et al. |
| 2017/0367766 A1 | 12/2017 | Mahfouz |
| 2017/0372504 A1 | 12/2017 | Jang |
| 2018/0003943 A1 | 1/2018 | Chan |
| 2018/0008371 A1 | 1/2018 | Manus |
| 2018/0042466 A1 | 2/2018 | Kang et al. |
| 2018/0047165 A1 | 2/2018 | Sato |
| 2018/0104009 A1 | 4/2018 | Abhari et al. |
| 2018/0125586 A1 | 5/2018 | Sela et al. |
| 2018/0130255 A1 | 5/2018 | Hazeghi et al. |
| 2018/0165823 A1 | 6/2018 | Ludwig |
| 2018/0168769 A1 | 6/2018 | Wood et al. |
| 2018/0174318 A1 | 6/2018 | Wang et al. |
| 2018/0199902 A1* | 7/2018 | Erhard .................. G06T 15/08 |
| 2018/0235715 A1 | 8/2018 | Amiot et al. |
| 2018/0243043 A1 | 8/2018 | Michihata et al. |
| 2018/0253593 A1 | 9/2018 | Hu et al. |
| 2018/0253909 A1 | 9/2018 | Chen et al. |
| 2018/0256264 A1 | 9/2018 | McLachlin et al. |
| 2018/0261009 A1 | 9/2018 | Tepper et al. |
| 2018/0276877 A1 | 9/2018 | Mountney et al. |
| 2019/0011703 A1 | 1/2019 | Robaina et al. |
| 2019/0053691 A1 | 2/2019 | Hansen et al. |
| 2020/0015893 A1 | 1/2020 | Walach |
| 2020/0110158 A1 | 4/2020 | Ecins et al. |
| 2020/0158874 A1 | 5/2020 | Li et al. |
| 2020/0305721 A1 | 10/2020 | Chen et al. |
| 2021/0030277 A1 | 2/2021 | Ferguson, Jr. et al. |
| 2021/0282654 A1 | 9/2021 | Cha et al. |
| 2022/0012954 A1 | 1/2022 | Buharin |
| 2022/0331558 A1* | 10/2022 | Averbuch .......... A61M 25/0147 |

FOREIGN PATENT DOCUMENTS

| | | |
|---|---|---|
| TW | 567693 B | 12/2003 |
| WO | WO-2010096447 A2 | 8/2010 |
| WO | WO-2010096453 A1 | 8/2010 |
| WO | WO-2012033578 A1 | 3/2012 |
| WO | WO-2012096878 A2 | 7/2012 |
| WO | WO-2014152753 A1 | 9/2014 |
| WO | WO-2014177604 A1 | 11/2014 |
| WO | WO-2016061052 A1 | 4/2016 |
| WO | WO-2016153741 A1 | 9/2016 |
| WO | WO-2017075602 A1 | 5/2017 |
| WO | WO-2017180097 A1 | 10/2017 |
| WO | WO-2018112424 A1 | 6/2018 |
| WO | WO-2019045971 A1 | 3/2019 |
| WO | WO-2020006454 A1 | 1/2020 |
| WO | WO-2020018931 A1 | 1/2020 |
| WO | WO-2020140044 A1 | 7/2020 |
| WO | WO-2021211986 A1 | 10/2021 |
| WO | WO-2022029308 A1 | 2/2022 |
| WO | WO-2022058499 A1 | 3/2022 |

OTHER PUBLICATIONS

Halmetschlager-Funek et al. An Empirical Evaluation of Ten Depth Cameras: Bias, Precision, Lateral Noise, Different Lighting Conditions and Materials, and Multiple Sensor Setups in Indoor Environments, IEEE Robotics & Automation Magazine pp. 99:1-1 Aug. 2018.
PCT/US19/42647 International Search Report dated Oct. 18, 2019.
PCT/US2021/02771 International Search Report & Written Opinion dated Sep. 17, 2021.
U.S. Appl. No. 17/150,701 Notice of Allowance dated Sep. 29, 2021.
U.S. Appl. No. 17/150,701 Office Action dated Jun. 21, 2021.
Co-pending U.S. Appl. No. 17/938,614, filed Oct. 6, 2022.
Dunn, et al. Laser speckle contrast imaging in biomedical optics. Journal of Biomedical Optics 15(1), 011109 (Jan./Feb. 2010).
EP19905077.4 Extended Search Report dated Aug. 8, 2022.
Holstein-Rathlou et al. Nephron blood flow dynamics measured by laser speckle contrast imaging. Am J Phsiol Renal Physiol 300: F319-F329, 2011.
PCT/US19/68760 Search Report & Written Opinion dated Apr. 1, 2020.
Richards et al. Intraoperative laser speckle contrast imaging with retrospective motion correction for quantitative assessment of cerebral blood flow. Neurophotonics 1(1), 015006 (Jul.-Sep. 2014).
Richards et al. Low-cost laser speckle contrast imaging of blood flow using a webcam. 2013 Optical Society of America.
U.S. Appl. No. 17/349,713 Office Action dated Aug. 12, 2022.
U.S. Appl. No. 17/349,713 Office Action dated Mar. 17, 2023.

* cited by examiner

Table 1. The analyzed sensors and their specifications given by the manufacturers.

| Sensor | Xtion Pro Live [2] | Structure IO [4] | Orbbec Pro [5] | Kinectv2 [6] | RS D435 [7] |
|---|---|---|---|---|---|
| Manufacturer | ASUS | Occipital, Inc. | Orbbec | Microsoft | Intel |
| Sensor type | RGBD | D | RGBD | RGBD | RGBD |
| Technology | Infrared pattern | Infrared pattern | Infrared pattern | ToF | Active stereo |
| Depth resolution | 640 × 480 | 640 × 480 | 640 × 480 | 512 × 424 | 1,280 × 720 |
| Range [m] | 0.8–3.5 | 0.4–3.5+ | 0.6–8 | 0.5–4.5 | 0.2–10 |
| Interface | USB 2 | USB 2 | USB 2 | USB 3 | USB 3 |

| Sensor | RS ZR300 [8] | RS R200 [9] | RS F200 [10] | RS SR300 [11] | Ensenso N35 [12] |
|---|---|---|---|---|---|
| Manufacturer | Intel | Intel | Intel | Intel | Ensenso |
| Sensor type | RGBD | RGBD | RGBD | RGBD | D |
| Technology | Active stereo | Active stereo | Infrared pattern | Infrared pattern | Active stereo |
| Depth resolution | 628 × 468 | 640 × 480 | 640 × 480 | 640 × 480 | 1,280 × 1,024 |
| Range (m) | 0.55–2.8 | 0.51–4 | 0.2–1.2 | 0.2–2 | 0.47–1.1 |
| Interface | USB 3 | USB 3 | USB 3 | USB 3 | Ethernet |

USB: universal serial bus.

Fig. 8

Table 2. The lateral noise.

| Sensor | Lateral Noise (Pixel) | | | |
|---|---|---|---|---|
| | d = 0-0.7 m | d = 0.7 m | d = 0.7-3 m | d = 3-5 m |
| Asus Xtion | — | — | 3 | 2 |
| Structure IO | — | — | 3 | 2 |
| Orbbec 3-D | — | — | 3 | 2 |
| Kinectv2 | — | — | 1 | 1 |
| D435 | 1 | — | 1 | 2 |
| ZR300 | — | — | 0.5-1.2 | 1 |
| R200 | — | — | 2-3 | — |
| F200 | 1.5 | — | — | — |
| SR300 | 2 | — | — | — |
| Ensenso | 3 | — | — | — |

Fig. 11

SYSTEMS AND METHODS FOR MULTI-MODAL SENSING OF DEPTH IN VISION SYSTEMS FOR AUTOMATED SURGICAL ROBOTS

CROSS-REFERENCE

This application is a continuation of U.S. patent application Ser. No. 17/150,701, filed on Jan. 15, 2021 and issued as U.S. Pat. No. 11,179,218, which application is a continuation application of International Application No. PCT/US2019/042647 filed on Jul. 19, 2019, which claims priority to U.S. Provisional Patent Application No. 62/700,700 filed on Jul. 19, 2018, which applications are incorporated herein by reference in their entirety for all purposes.

BACKGROUND

Embodiments of the present disclosure generally relate to multi-modal sensing of three-dimensional position information of a surface of an object.

SUMMARY

According to embodiments of the present disclosure, systems for, methods for, and computer program products for determining a three-dimensional coordinate on an object are provided. In the method, an image is recorded. The image includes an object, a first plurality of markers disposed on the object, a second plurality of markers disposed on the object, and a third plurality of markers disposed on the object. A first depth is computed using the image and the first plurality of markers. A second depth is computed using the image and the second plurality of markers. A third depth is computed using the image and the third plurality of markers. A first weight is assigned to the first depth, a second weight is assigned to the second depth, and a third weight is assigned to the third depth. A weighted average depth is computed based on the first depth, second depth, third depth, first weight, second weight, and third weight.

In various embodiments, a system is provided for determining a three-dimensional coordinate on an object. The system includes an imaging device and a computing node including a computer readable storage medium having program instructions embodied therewith. The program instructions are executable by a processor of the computing node to cause the processor to perform a method where an image is recorded by the imaging device. The image includes an object, a first plurality of markers disposed on the object, a second plurality of markers disposed on the object, and a third plurality of markers disposed on the object. A first depth is computed using the image and the first plurality of markers. A second depth is computed using the image and the second plurality of markers. A third depth is computed using the image and the third plurality of markers. A first weight is assigned to the first depth, a second weight is assigned to the second depth, and a third weight is assigned to the third depth. A weighted average depth is computed based on the first depth, second depth, third depth, first weight, second weight, and third weight.

In various embodiments, a computer program product is provided for determining a three-dimensional coordinate on an object. The computer program product includes a computer readable storage medium having program instructions embodied therewith. The program instructions are executable by a processor to cause the processor to perform a method where an image is recorded. The image includes an object, a first plurality of markers disposed on the object, a second plurality of markers disposed on the object, and a third plurality of markers disposed on the object. A first depth is computed using the image and the first plurality of markers. A second depth is computed using the image and the second plurality of markers. A third depth is computed using the image and the third plurality of markers. A first weight is assigned to the first depth, a second weight is assigned to the second depth, and a third weight is assigned to the third depth. A weighted average depth is computed based on the first depth, second depth, third depth, first weight, second weight, and third weight.

In various embodiments, systems for, methods for, and computer program products for determining a three-dimensional coordinate on an object are provided. In the method, an image is recorded. The image includes an object, a first plurality of markers disposed on the object, and a second plurality of markers disposed on the object. A first depth is computed using the image and the first plurality of markers. A second depth is computed using the image and the second plurality of markers. A first weight is assigned to the first depth and a second weight is assigned to the second depth. A weighted average depth is computed based on the first depth, second depth, first weight, and second weight.

In various embodiments, an integrated surgical device is provided including an endoscope having a proximal end and a distal end, an imaging device optically coupled to the distal end of the endoscope, and a computing node comprising a computer readable storage medium having program instructions embodied therewith. The program instructions are executable by a processor of the computing node to cause the processor to perform a method where an image is recorded. The image includes an object, a first plurality of markers disposed on the object, a second plurality of markers disposed on the object, and a third plurality of markers disposed on the object. A first depth is computed using the image and the first plurality of markers. A second depth is computed using the image and the second plurality of markers. A third depth is computed using the image and the third plurality of markers. A first weight is assigned to the first depth, a second weight is assigned to the second depth, and a third weight is assigned to the third depth. A weighted average depth is computed based on the first depth, second depth, third depth, first weight, second weight, and third weight.

BRIEF DESCRIPTION OF THE DRAWINGS

FIG. 8 shows a table of analyzed sensors and their specifications according to embodiments of the present disclosure.

FIG. 11 shows a table of lateral noise of various sensors according to embodiments of the present disclosure.

DETAILED DESCRIPTION

Figure 1:
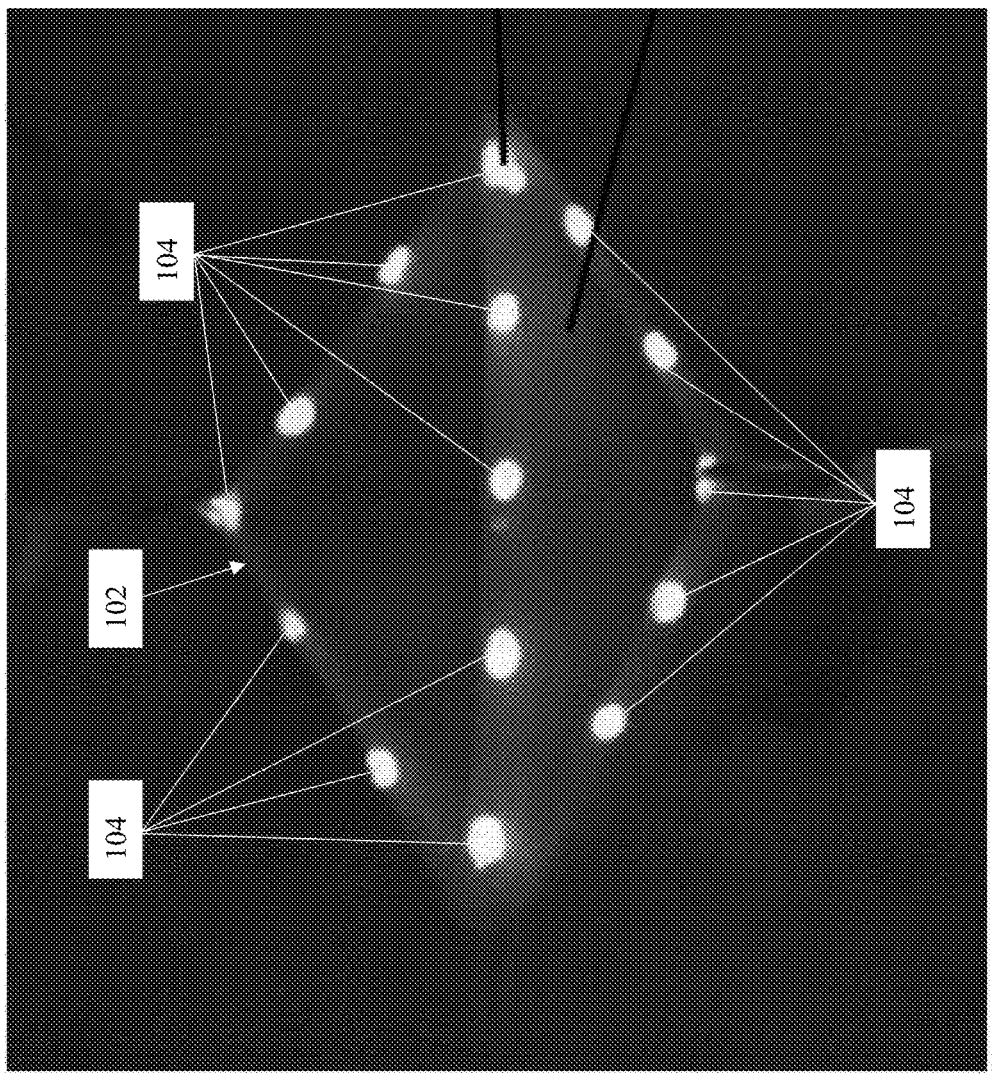
FIG. 1 illustrates an exemplary image of a surface having fiducial markers in which the image may be used as a baseline image according to embodiments of the present disclosure.

The ability to accurately discern three-dimensional position information (X, Y, Z) of target objects (e.g., biological tissue) is a necessary and critical requirement of an automated surgical robotic system. One approach is to use fiducial markers of a known size and shape directly attached to a surface of an object to determine positional information about the surface; however, spatial resolution of any method using fiducial markers is limited to the number of fiducials applied to the tissue. Fiducial markers must be large enough for computer vision systems to detect, but also small enough to maximize spatial resolution of the surface to which they are attached. Because of these conflicting requirements, there is an upper bound to the spatial resolution provided by fiducial markers, especially in surgical settings where automated surgical robot systems may be operating in small, confined spaces.

Many surgical maneuvers (e.g., suturing) require highly dexterous and highly accurate motion of surgical tools to achieve a satisfactory surgical outcome. In fully automated robotic surgical procedures having no active human control, the accuracy of the surgical tools controlled by the robot is highly dependent on the spatial resolution of the computer vision system. Because surgical outcomes are heavily dependent on the positional accuracy of the computer vision systems guiding the robotic tools, spatial resolution of the surgical sites is even more important in fully automated robotic surgical procedures. Solely using fiducial markers to guide fully automate surgical robots does not provide adequate spatial resolution of surgical sites to ensure satisfactory outcomes.

Accordingly, a need exists for a system and method to accurately and reliably sense positional information with a high resolution which enables accurate surgical planning and execution to improve enable robotic-assisted surgery.

Embodiments of the present disclosure generally relate to multi-modal sensing of three-dimensional position information of a surface of an object. In particular, the present disclosure describes multiple visualization modalities used to collect distinctive positional information of the surface of the object that is then combined using weighting factors to compute a final three-dimensional position. While the present disclosure generally focuses on sensing three-dimensional position with respect to automated surgical robots, the systems, methods, and computer program products are suitable for use in other fields that employ computer vision techniques to identify three-dimensional position, such as virtual reality or augmented reality applications.

A system for determining a three-dimensional coordinate on a surface of an object (e.g., a biological tissue) generally includes a first imaging system used to establish a baseline image of the object. The baseline image may be established using, e.g., a series of fiducial markers affixed to the surface of the object, to generate positional information for the surface of the object. For example, fiducial markers may be placed on the surface of a tissue via a spray applicator (e.g., spray catheter) In general, fiducial markers are special markers that may be recognized by a computer vision system to determine specific position information about the surface to which they are affixed. Non-limiting examples of fiducial markers may include symbols (e.g., alphanumeric), patterns (e.g., QR codes), liquid (e.g., infrared ink), or physical shapes (2D or 3D). This position information may be used to map the surface of the object and create a computer simulation of that surface in three-dimensions. The fiducial markers may be affixed to the object in a particular pattern (e.g., a grid pattern) or no particular pattern (e.g., randomized placement).

In various embodiments, the fiducial marker is applied to target tissue in a liquid state through a syringe needle. Applying a liquid marker to target tissue has a number of advantages. First, the marker can be mixed onsite which improves the stability of the marker. Second, a liquid marker allows the precise control over location and application to target tissue. Third, the marker can be applied as any irregular shape. By applying a liquid marker with syringe, the irrigated surgical field causes an exothermic reaction to solidify the marker in a circular shape to target tissue. A circular marker may be beneficial for tracking single points of interest on target tissue during a surgical procedure.

In various embodiments, a marking tip such as a syringe needle or felt nib may be used to dispense the fiducial marker in a linear pattern. By applying the fiducial marker as a continuous line, one can use the marker to define boundaries on target tissue. Defining boundaries may be useful to identify regions of diseased tissue or regions where a surgical procedure should not be performed. In yet another embodiment, the liquid marker may be sprayed onto the target tissue to create a speckled pattern when polymerized. A speckled pattern may be of interest to define large regions of tissue from each other. In one example, background tissue may be speckled to distinguish it from foreground tissue. Other components in robotic or semi-autonomous workflow may use background and foreground information to plan or control their motions or suggestions.

In other embodiments, the liquid marker may be applied though a predefined mask to apply the marker in any arbitrary and predefined shape on target tissue.

To acquire the position information of the surface of the object using fiducial markers, the first imaging system may include one or more cameras (e.g., one, two, three, four, or five). In various embodiments, the one or more cameras may include a stereoscopic camera. In various embodiments, the stereoscopic camera may be implemented by two separate cameras. In various embodiments, the two separate cameras may be disposed at a predetermined distance from one another. In various embodiments, the stereoscopic camera may be located at a distal-most end of a surgical instrument (e.g., laparoscope, endoscope, etc.). The camera(s) may cross-reference detected positions for each of the fiducial markers against a known reference (e.g., the known size and shape of the fiducial) to determine a positional information (e.g., depth) for each of the fiducial markers. Positional information, as used herein, may generally be defined as (X, Y, Z) in a three-dimensional coordinate system.

The one or more cameras may be, for example, infrared cameras, that emit infrared radiation and detect the reflection of the emitted infrared radiation. In other embodiments, the one or more cameras may be digital cameras as are known in the art. In other embodiments, the one or more cameras may be plenoptic cameras. The one or more cameras may be connected to a computing node as described in more detail below.

The present disclosure improves on the single mode approaches employing solely fiducial markers by also incorporating other visualization modalities in addition to fiducial marker tracking to improve the accuracy of the resulting positional information. A second imaging system may be used to generate position information for the surface of the object either individually or in combination with the other imaging systems described herein (e.g., after a baseline image is recorded using the first imaging system and positional information is acquired for each of the fiducial markers). The structured pattern projected from the structured light source may change shape, size, and/or spacing of pattern features when projected on a surface. The second imaging system may detect these changes and determine positional information based on the changes to the structured light pattern given a known pattern stored by the second imaging system. For example, the second imaging system may include a structured light source (e.g., a projector) that projects a specific structured pattern of lines (e.g., a matrix of dots or a series of stripes) onto the surface of the object. The pattern of lines produces a line of illumination that appears distorted from other perspectives than that of the source and these lines can be used for geometric reconstruction of the surface shape, thus providing positional information about the surface of the object.

The second imaging system may include one or more cameras (e.g., one, two, three, four, or five) capable of detecting the projected pattern from the source of structured light. The one or more cameras may be digital camera(s) as are known in the art and may be the same or different camera(s) as used with the first imaging system. The one or more cameras may be connected to a computing node as described in more detail below. Using the images from the one or more cameras, the computing node may compute positional information (X, Y, Z) for any suitable number of points along the surface of the object to thereby generate a depth map of the surface.

A third imaging system may be used to generate additional position information for the surface of the object. The third imaging system may include one or more cameras, such as a light-field camera (e.g., a plenoptic camera), and may be the same or different camera(s) as the camera(s) used for the first imaging system and the second imaging system. The plenoptic camera may be used to generate accurate positional information for the surface of the object by having appropriate zoom and focus depth settings.

One type of light-field (e.g., plenoptic) camera that may be used according to the present disclosure uses an array of micro-lenses placed in front of an otherwise conventional image sensor to sense intensity, color, and directional information. Multi-camera arrays are another type of light-field camera. The "standard plenoptic camera" is a standardized mathematical model used by researchers to compare different types of plenoptic (or light-field) cameras. By definition the "standard plenoptic camera" has micro lenses placed one focal length away from the image plane of a sensor. Research has shown that its maximum baseline is confined to the main lens entrance pupil size which proves to be small compared to stereoscopic setups. This implies that the "standard plenoptic camera" may be intended for close range applications as it exhibits increased depth resolution at very close distances that can be metrically predicted based on the camera's parameters. Other types/orientations of plenoptic cameras may be used, such as focused plenoptic cameras, coded aperture cameras, and/or stereo with plenoptic cameras.

Once positional information is generated using the first imaging system, the second imaging system and the third imaging system, a combined position may be calculated by computing a weighted average of the three imaging systems. As shown below in Equation 1, a combined pixel depth may be calculated by a weighted average of the depth generated from each of the three imaging systems.

$$\text{pixel depth} = \frac{C_M}{C_M + C_{SL} + C_P} * \text{Depth}_M + \frac{C_{SL}}{C_M + C_{SL} + C_P} * \text{Depth}_{SL} + \frac{C_P}{C_M + C_{SL} + C_P} * \text{Depth}_P \quad \text{(Eqn. 1)}$$

In Equation 1, $C_M$ represents the weight assigned to the first imaging system (e.g., the marker-based system), $C_{SL}$ represents the weight assigned to the second imaging system (e.g., the structured light-based system), $C_P$ represents the weight assigned to the third imaging system (e.g., the structured light-based system), $\text{Depth}_M$ represents the depth of the pixel generated from the first imaging system, $\text{Depth}_{SL}$ represents the depth of the pixel generated from the second imaging system, and $\text{Depth}_P$ represents the depth of the pixel generated from the third imaging system. In various embodiments, each of the weights may be a value between zero (0) and one (1), and the sum of all weight values may add up to unity (1).

In various embodiments, the weight $C_M$ assigned to the first imaging system may be equal to the weight $C_{SL}$ assigned to the second imaging system and the weight $C_P$ assigned to the third imaging system. In other embodiments, the weight $C_{SL}$ assigned to the second imaging system is greater than the weight $C_M$ assigned to the first imaging system and/or the weight $C_P$ assigned to the third imaging system. In yet another embodiment, the weight $C_P$ assigned to the third imaging system is greater than the weight $C_M$ assigned to the first imaging system and/or the weight $C_{SL}$ assigned to the second imaging system.

In various embodiments, weight for each variable in Equation 1 may be determined based on one or more factors selected based on the type of imaging system(s) used. For example, if light field imaging is used, factors may include: (1) amount of contrast in the image, (2) number of saturated pixels (which may be used to measure light intensity), and (3) localized change in depth of a specific area of the image. A high weight value may correspond to an image having high contrast within a scene, little to no saturated pixels, and low local change in depth.

In another example, if structured light imaging is used, factors may include: (1) amount of pattern recognized and (2) number of saturated pixels. A high weight value may correspond to an image having most or all of a pattern recognized and little to no saturated pixels.

In yet another example, if fiducial markers are used, factors may include (1) number of saturated pixels, (2) ability to recognize the shape/size of fiducial marker(s), and (3) ability to discern the fiducial marker(s) from the surrounding environment. A high weight value may correspond to an image having little to no saturated pixels, ability to recognize most or all of the fiducial markers, and the ability to discern the fiducials from the surrounding environment.

In various embodiments, any combination of two imaging modalities described herein may be used to compute first and second depths of a surface of an object. In this embodiment, each of the two imaging modalities may have a respective weighting factor that is applied to the depth determined by that particular modality. In various embodiments, the two weighting factors may add up to unity. In various embodiments, the pixel depth function is computed in a similar manner to that described above in Equation 1, but in contrast, the pixel depth for two modalities is dependent on only two weighted depth computations (instead of three).

In various embodiments, the weights associated with each imaging system may be dependent on the overall quality of the particular imaging system. For example, one particular imaging system may provide more accurate data overall than another imaging system. In this example, the data received the imaging system with the higher accuracy would be given a higher weight than the data received from the imaging system with the lower accuracy. In various embodiments, the accuracy and/or precision of various imaging systems may be dependent on the distance away from the object to be imaged, the material being imaged, and/or the lighting of the operating environment. In various embodiments, the accuracy and/or precision of various imaging systems may be dependent on a location in the field of view of the imaging system—for example a first imaging system may have high accuracy at the center of the field of view with a rapid decline towards the edges, while another imaging system may have a consistent accuracy across the field of view.

Figure 9A:
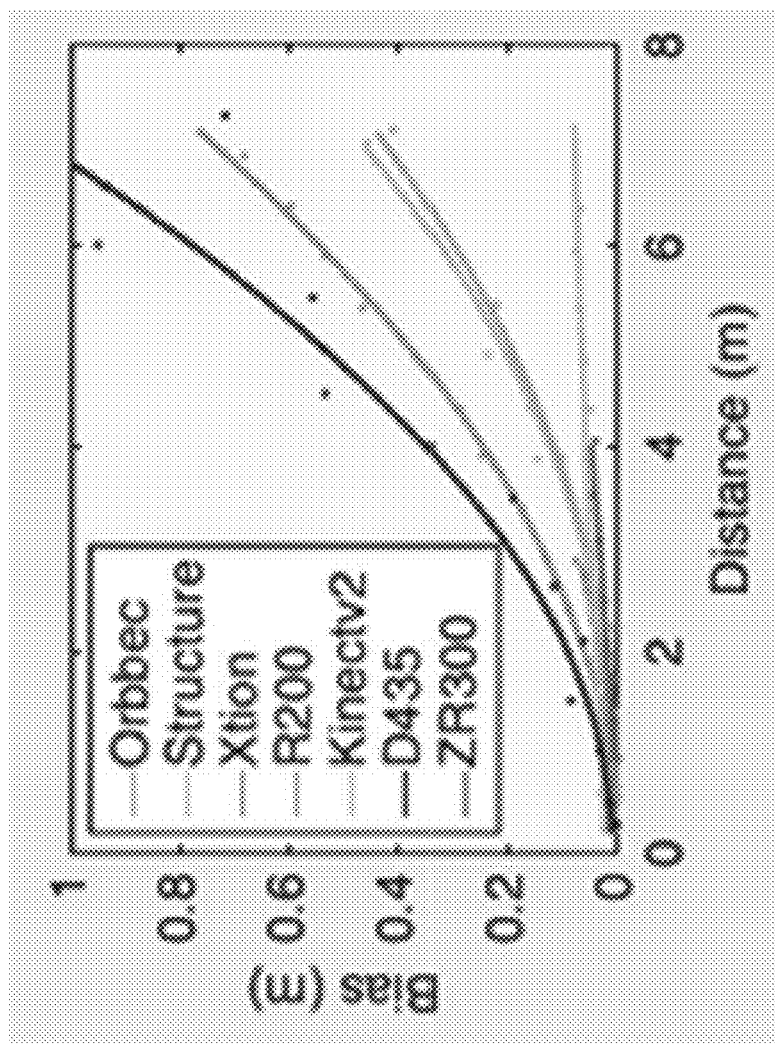
FIGS. 9A, 9B, and 9C illustrate graphs of the results of sensor bias according to embodiments of the present disclosure.
Figure 9B:
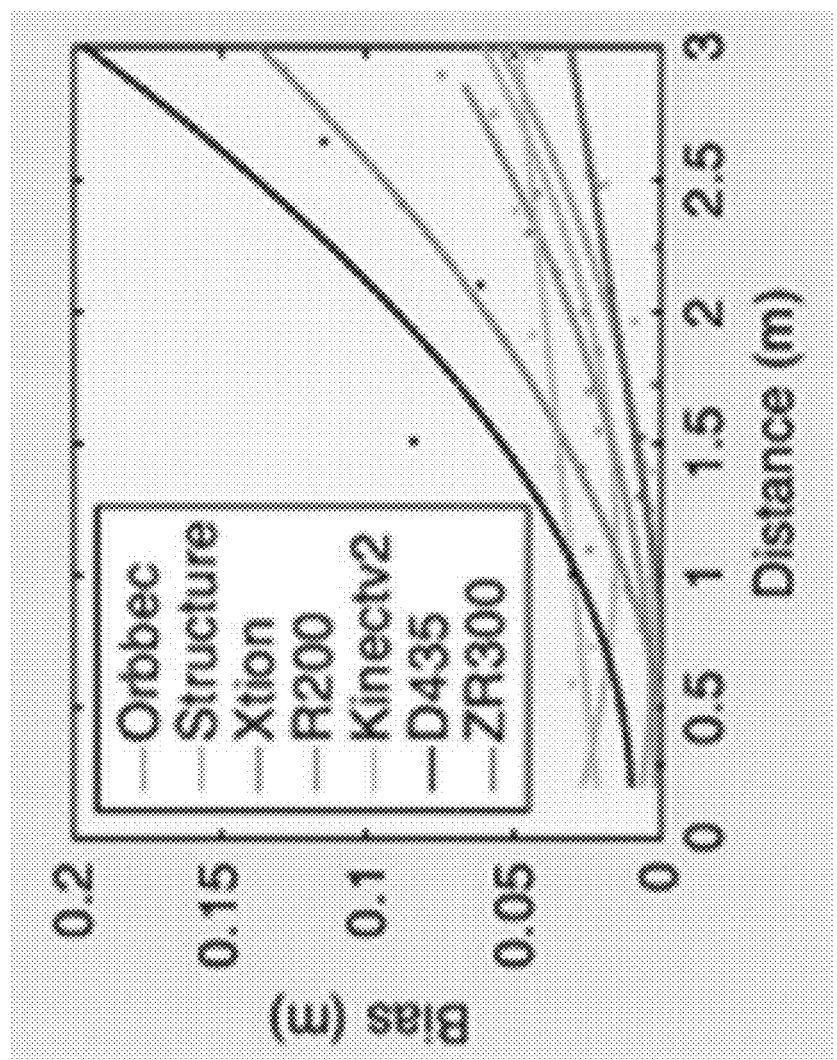
Figure 9C:
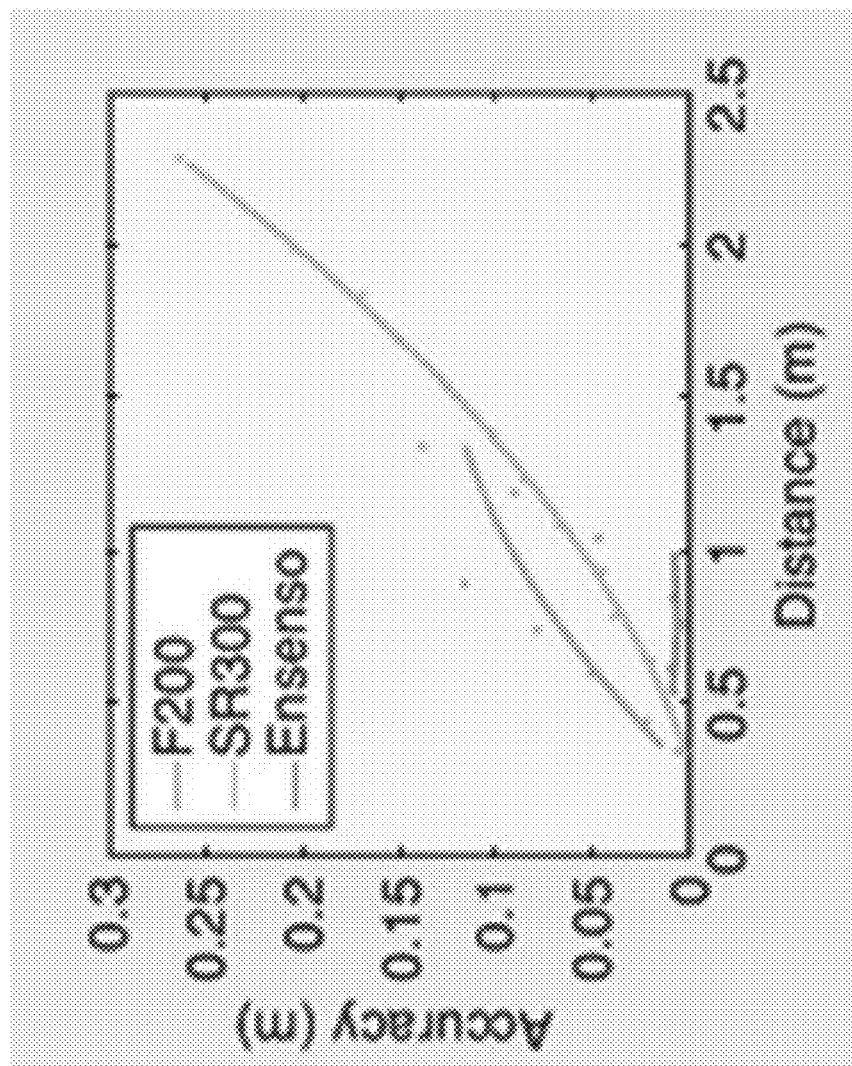

A discussion of how various sensors perform in different situations can be found in "An Empirical Evaluation of Ten Depth Cameras" by Halmetschlager-Funek et al., which is hereby incorporated by reference in its entirety. FIG. 8 shows a table of analyzed sensors in the Halmetschlager-Funek paper. FIGS. 9A, 9B, 9C, 10A, 10B, 10C, 11, 12A, 12B, 12C, 12D, 13A, 13B, 14A, 14B, and 14C illustrate various graphs from the Halmetschlager-Funek paper regarding the bias, precision, lateral noise, effects of materials/lighting/distance, and effects of additional sensors. In particular, regarding bias (shown in FIGS. 9A, 9B, and 9C), the paper describes that while the Kinectv2 offers low bias over the whole range, a significant increase of the bias for sensors using structured light was observed starting from d>3 m. While all three structured light sensors and the two active stereo cameras (ZR300 and D435) offer a lower bias than the Kinectv2 for distances d<1 m, three sensors (ZR300, Orbbec, and Structure IO) offer an even lower bias for depth values d<2.5 m. A quadratic increase of the bias was observed for all sensors [full range: d=0-8 m, FIG. 9A; zoom in: d=0-3 m, FIG. 9B]. The near-range sensors, F200 and SR300 [FIG. 9C], show a slightly higher bias than their far-range counterparts, while the Ensenso N35 provides a low bias over the whole measurement range.

Figure 10A:
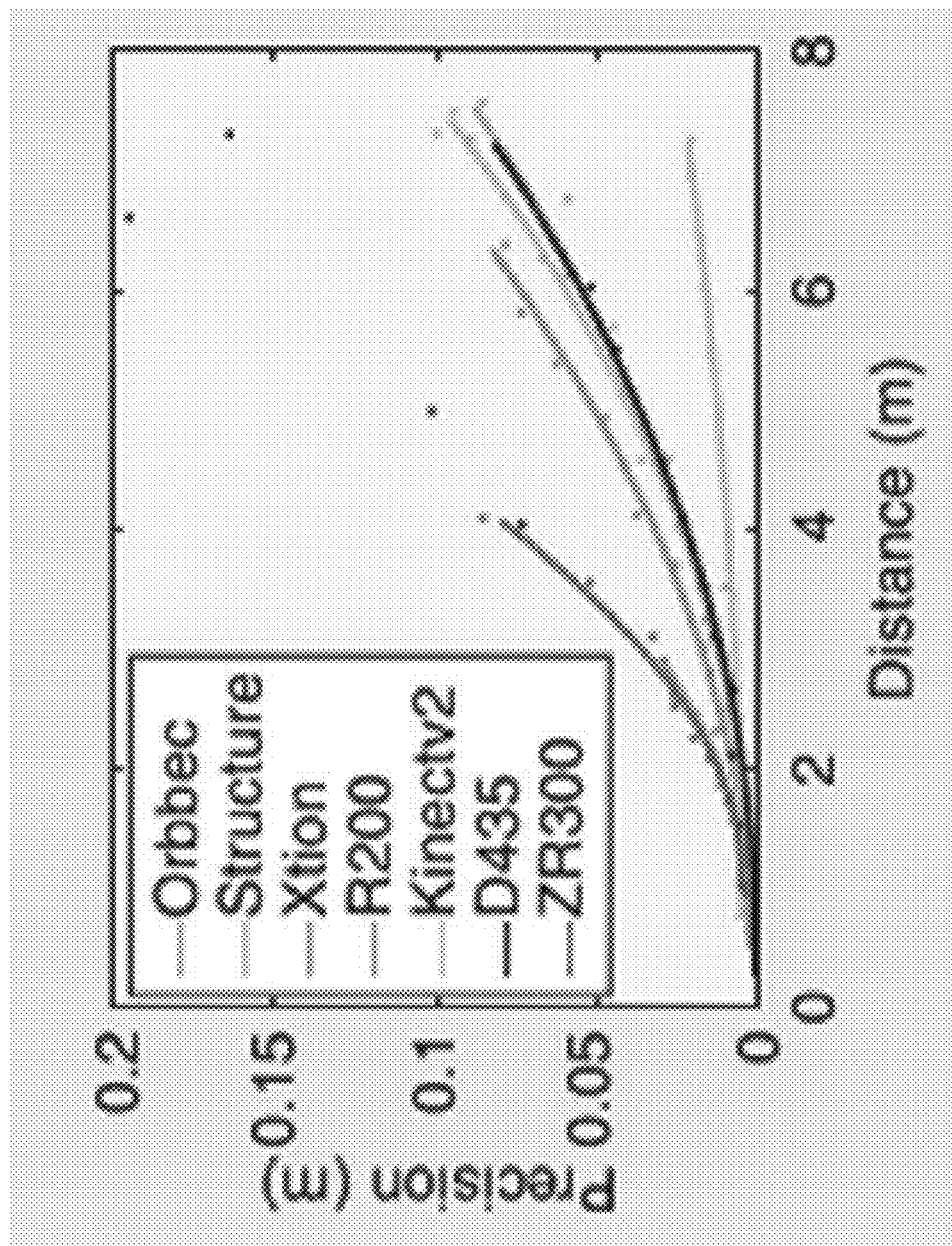
FIGS. 10A, 10B, and 10C illustrate graphs of the results of sensor precision according to embodiments of the present disclosure.
Figure 10B:
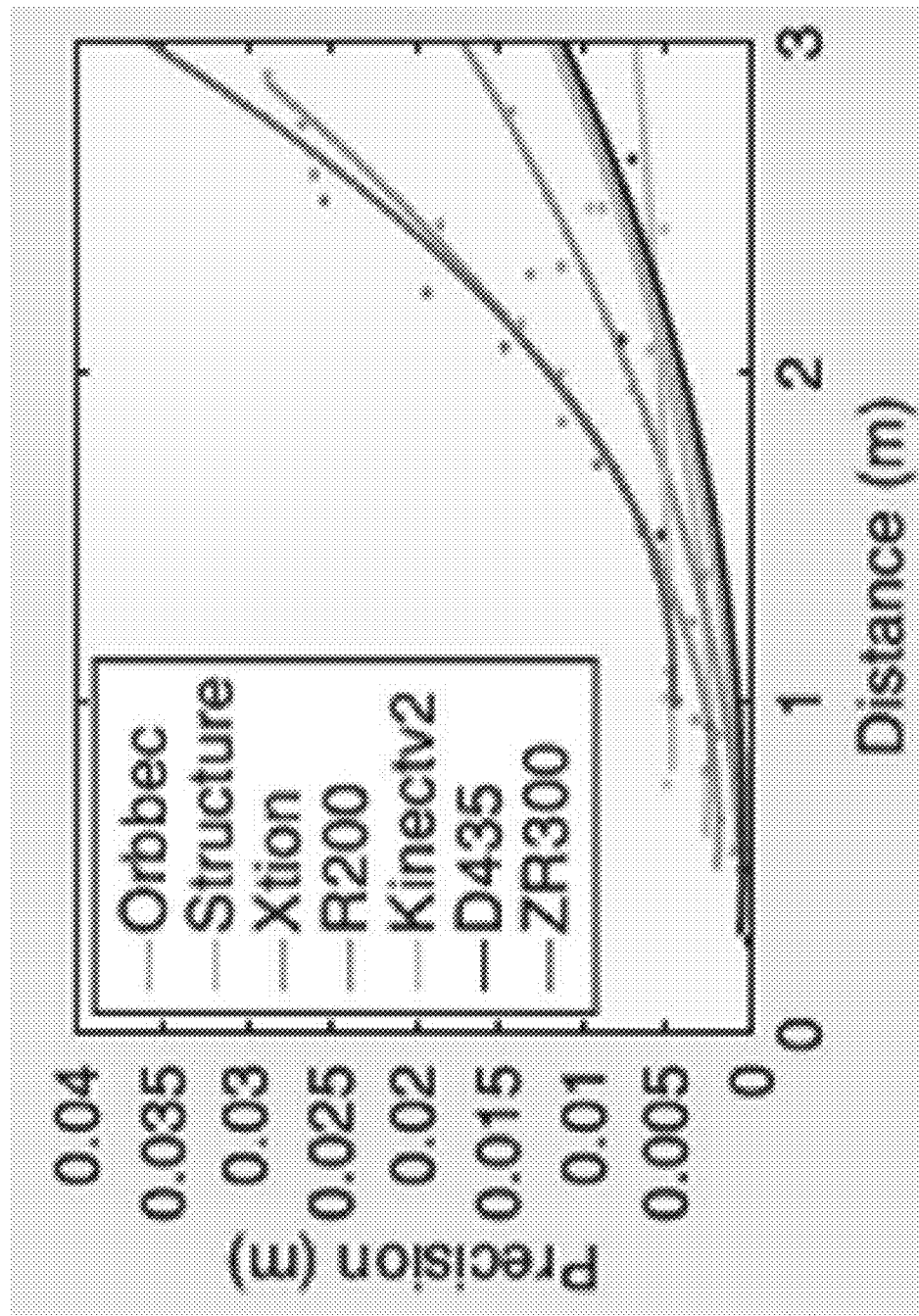
Figure 10C:
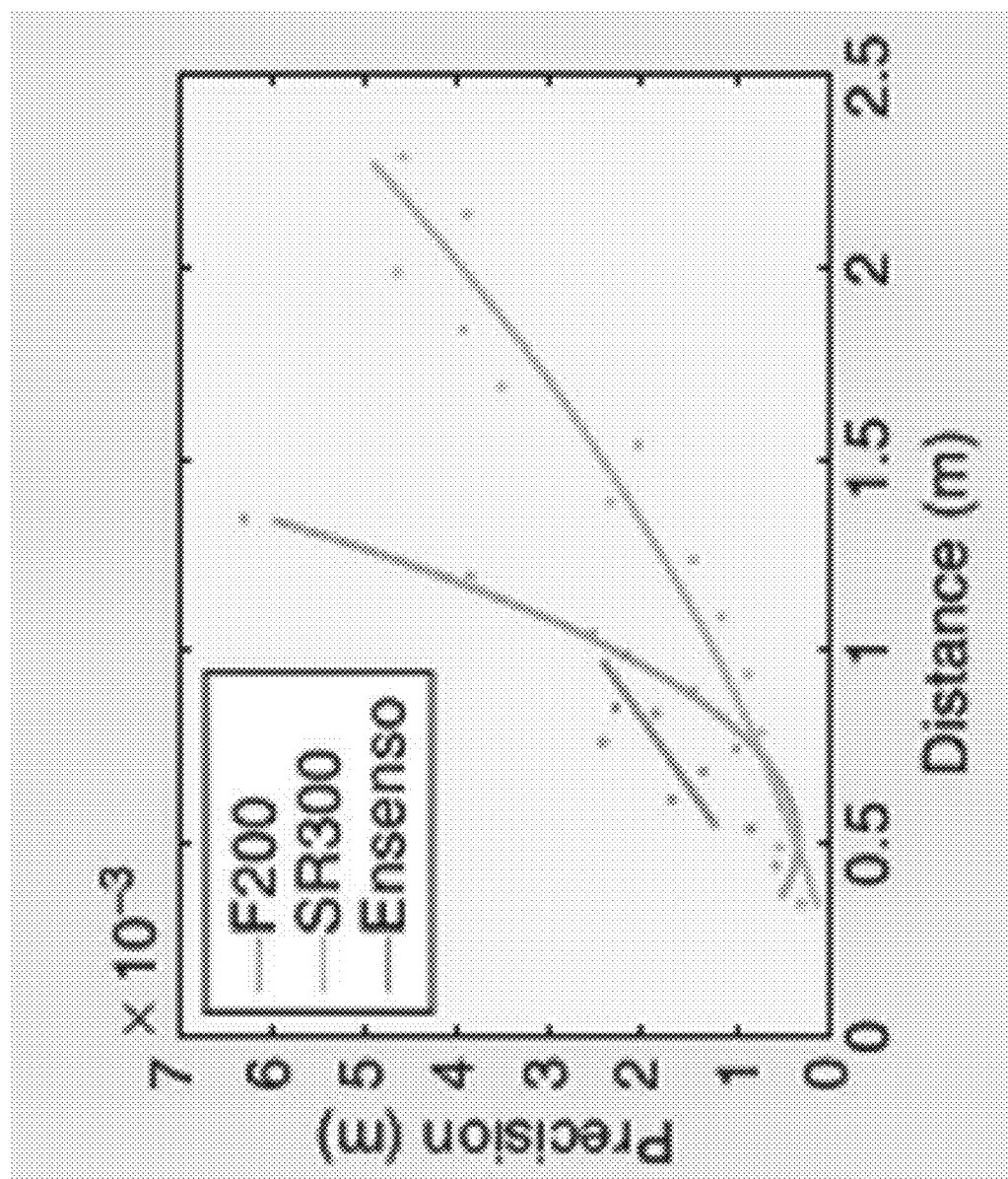
Figure 12A:
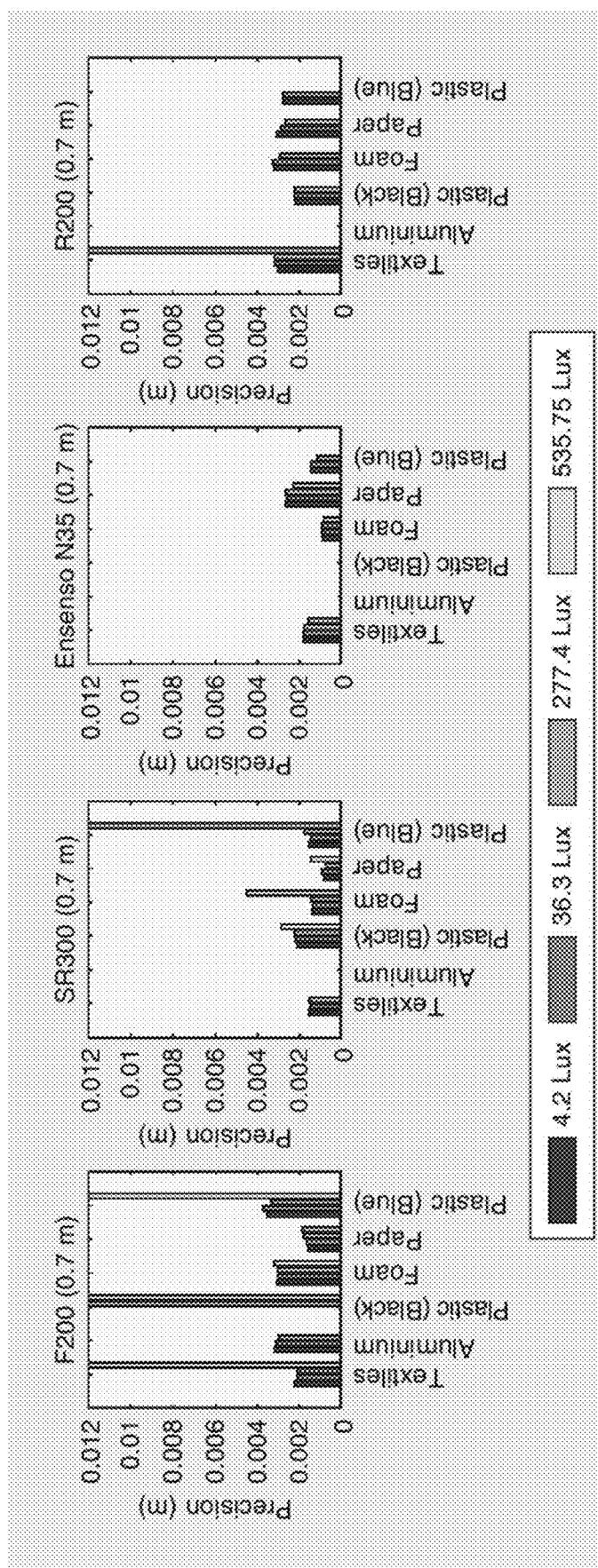
FIGS. 12A, 12B, 12C, and 12D illustrate graphs of the precision ratios for different materials and lighting conditions (lower is better) according to embodiments of the present disclosure.
Figure 12B:
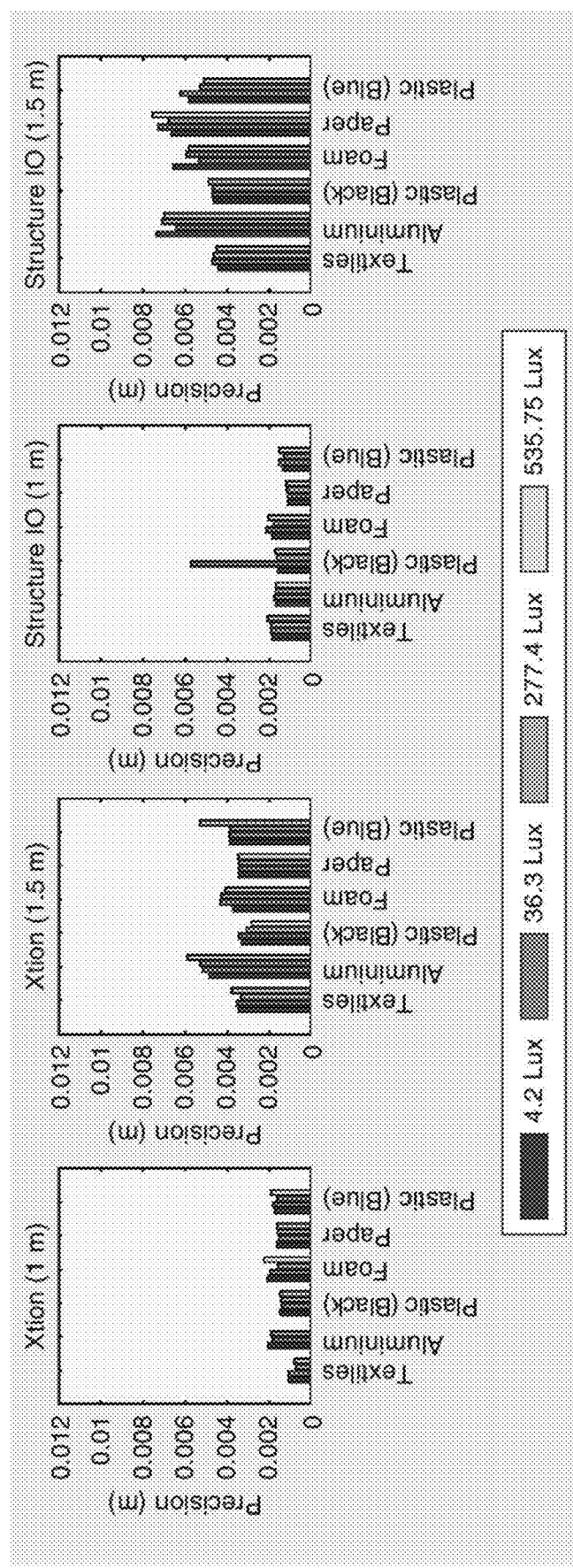
Figure 12C:
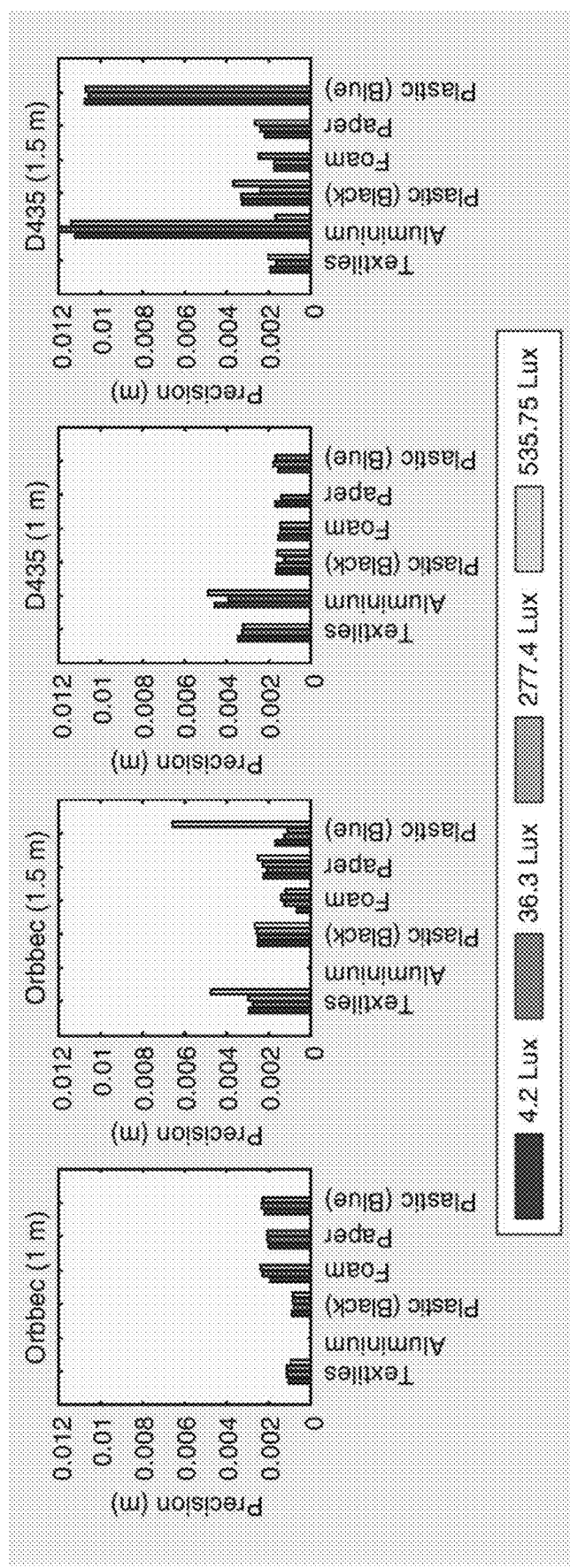
Figure 12D:
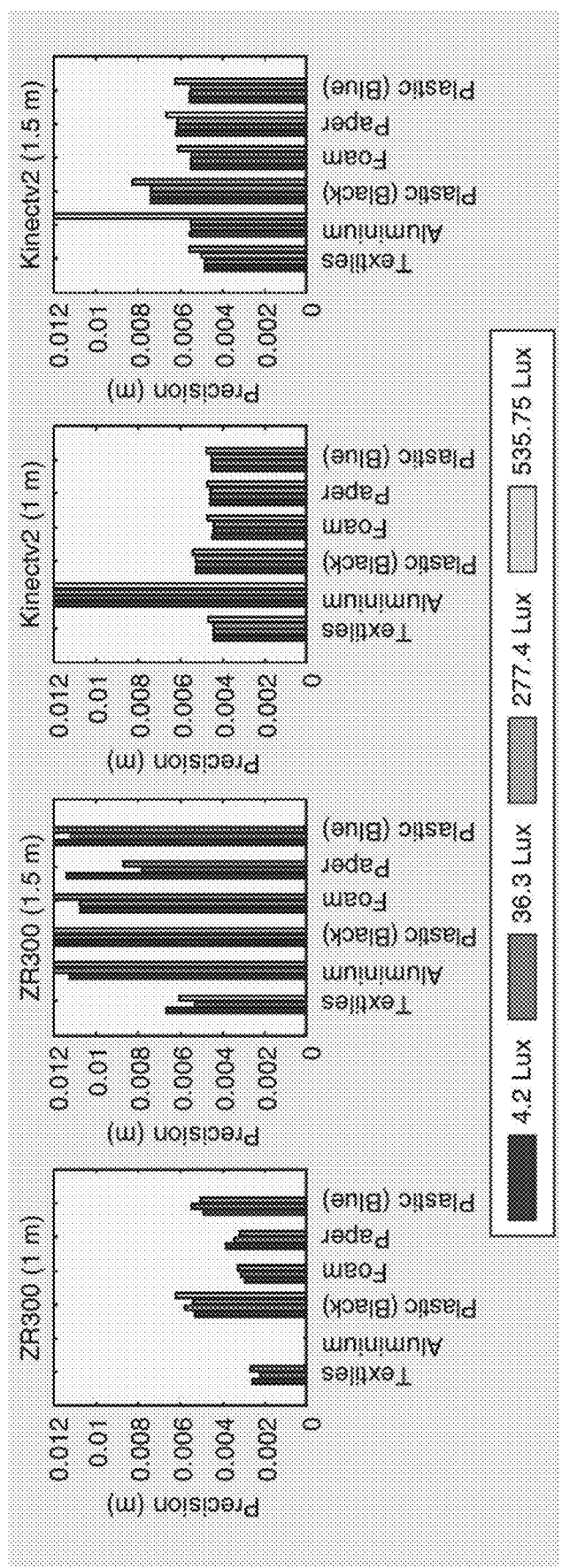
Figure 13A:
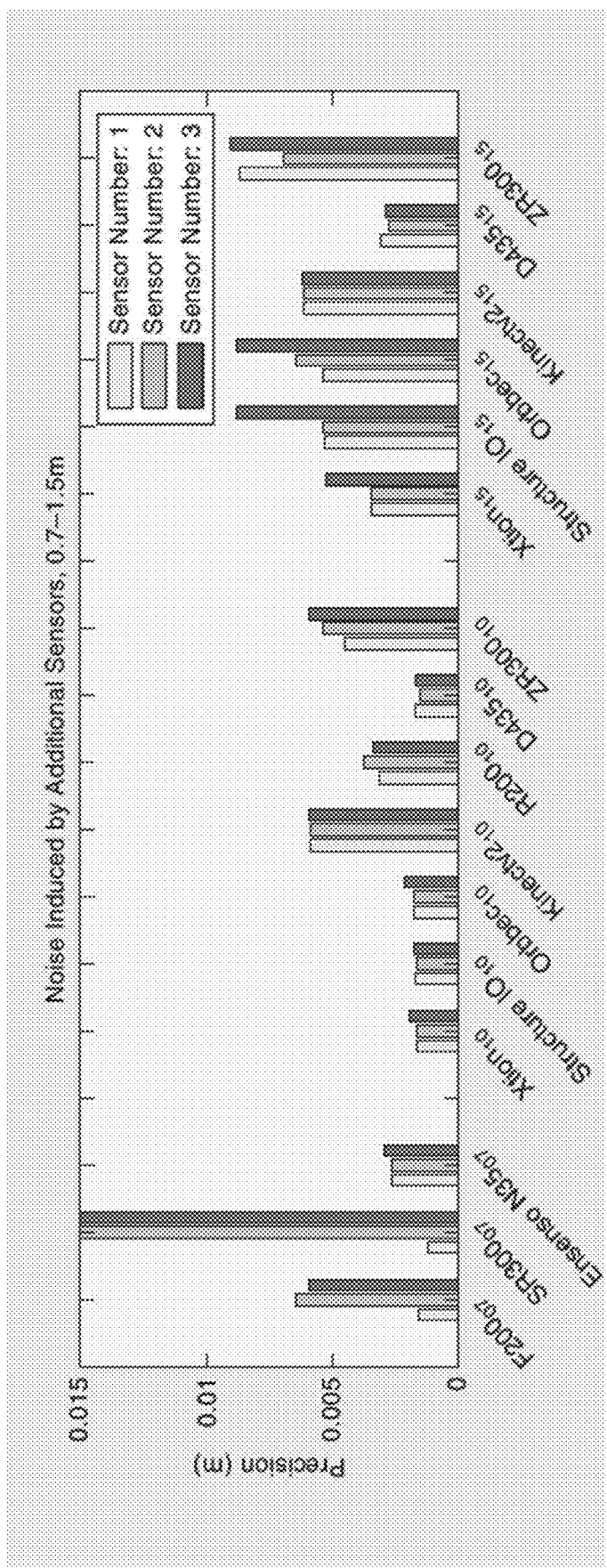
FIG. 13A illustrates a graph of the precision and FIG. 13B illustrates a graph of nan ratios (lower is better) in multi sensor setups where the indices represent the distance to the target according to embodiments of the present disclosure.
Figure 13B:
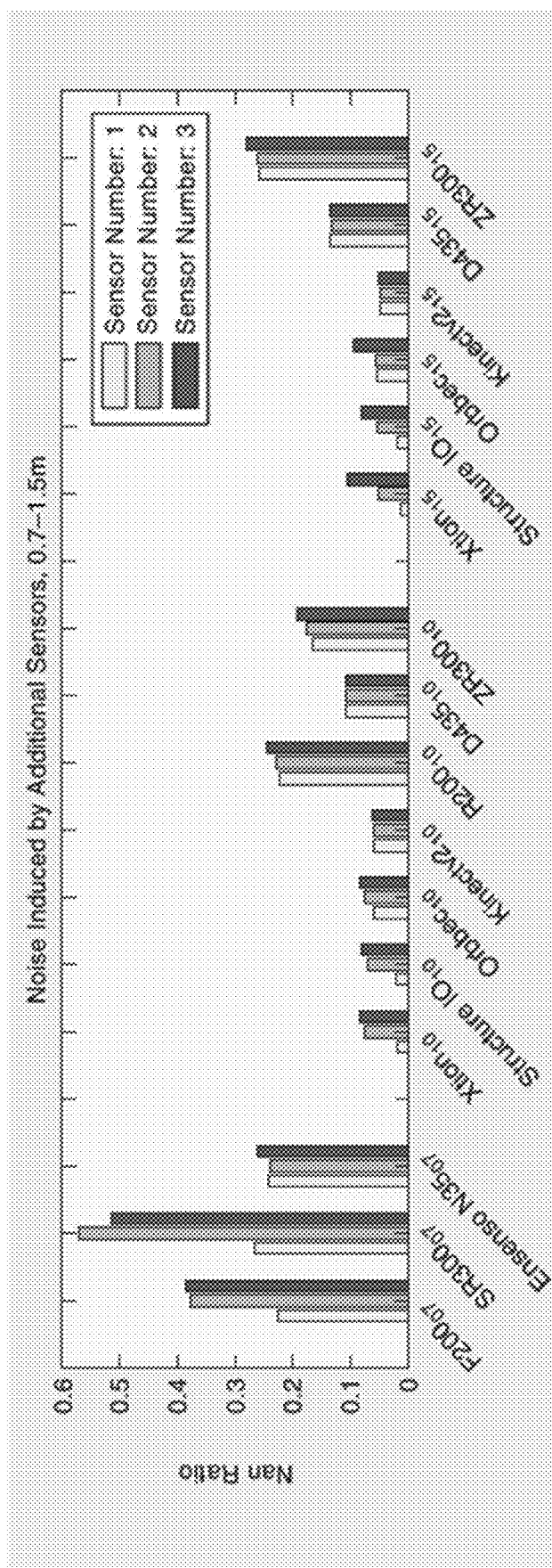

As for precision (as shown in FIGS. 10A, 10B, and 10C), a quadratic decrease of precision was found in all far-range sensors [full range: d=0-8 m, FIG. 10A; zoom in: d=0-3, m, FIG. 10B], but the structured light sensors differ in scale compared to the Kinectv2. Overall, the R200 and ZR300 sensors have the worst performance, while the Structure IO and Orbbec sensors perform very similarly. At distances d<2 m, all structured light sensors were observed to generate less noisy measurements than the Kinec-tv2. Moreover, the D435 was able to gather more precise results than the Kinectv2 at distances d<1 m. The precision results for the D435 were observed to be more scattered than for the other sensors. The near-range sensors [FIG. 10C] experience noise levels up to 0.0007 m. In the ranges specified by the manufacturers, precision values under 0.004 m were able to be obtained.

As for lateral noise (FIG. 11), the analysis of lateral noise shows similar results for the three far-range structured light sensors and distances. For d<3 m, the noise level was independent of the distance, with three pixels for the structured light sensors and one for the Kinectv2 (FIG. 11). Two active stereo sensors (D435 and ZR300) offer a low lateral noise level similar to that of the Kinectv2. The R200 achieves a lower lateral noise of two pixels for distances closer than 2 m. In the near-range sensor, the Ensenso N35 achieves the highest lateral noise value.

As for materials/lighting/distance (FIGS. 12A, 12B, 12C, and 12D), a total of 384 data points were gathered to determine how the sensors' precision was influenced by the reflection and absorption properties of six different materials in combination with four different lighting conditions from 4.2 to 535.75 lux (FIGS. 12A, 12B, 12C, and 12D). The tests reveal that the Structure 10 sensor best handles the varying object reflectances and lighting conditions. Although it has a lower precision compared to the other sensors for distances of d>1.5 m, it was able to gather information for high-reflective surfaces, such as aluminum, and under bright lighting conditions. While the Structure 10 sensor gives a dense depth estimation, the Xtion was not able to determine a depth value. The Orbbec may fail to gather depth information for four of the six surfaces under bright lighting conditions. The Kinectv2 may fails to gather reliable depth data for aluminum at distances of d=1 m and d=1.5 m and under bright lighting conditions. The F200 and SR300 sensors may have a significantly lower precision for bright lighting conditions. During the setup of the experiments, the active stereo cameras (Ensenso and R200) were expected to be able to handle different lighting conditions better than the structured light sensors due to the nature of their technology. In FIGS. 12A, 12B, 12C, and 12D, a precision of zero indicates that the sensor is not able to gather any depth information.

Figure 14A:
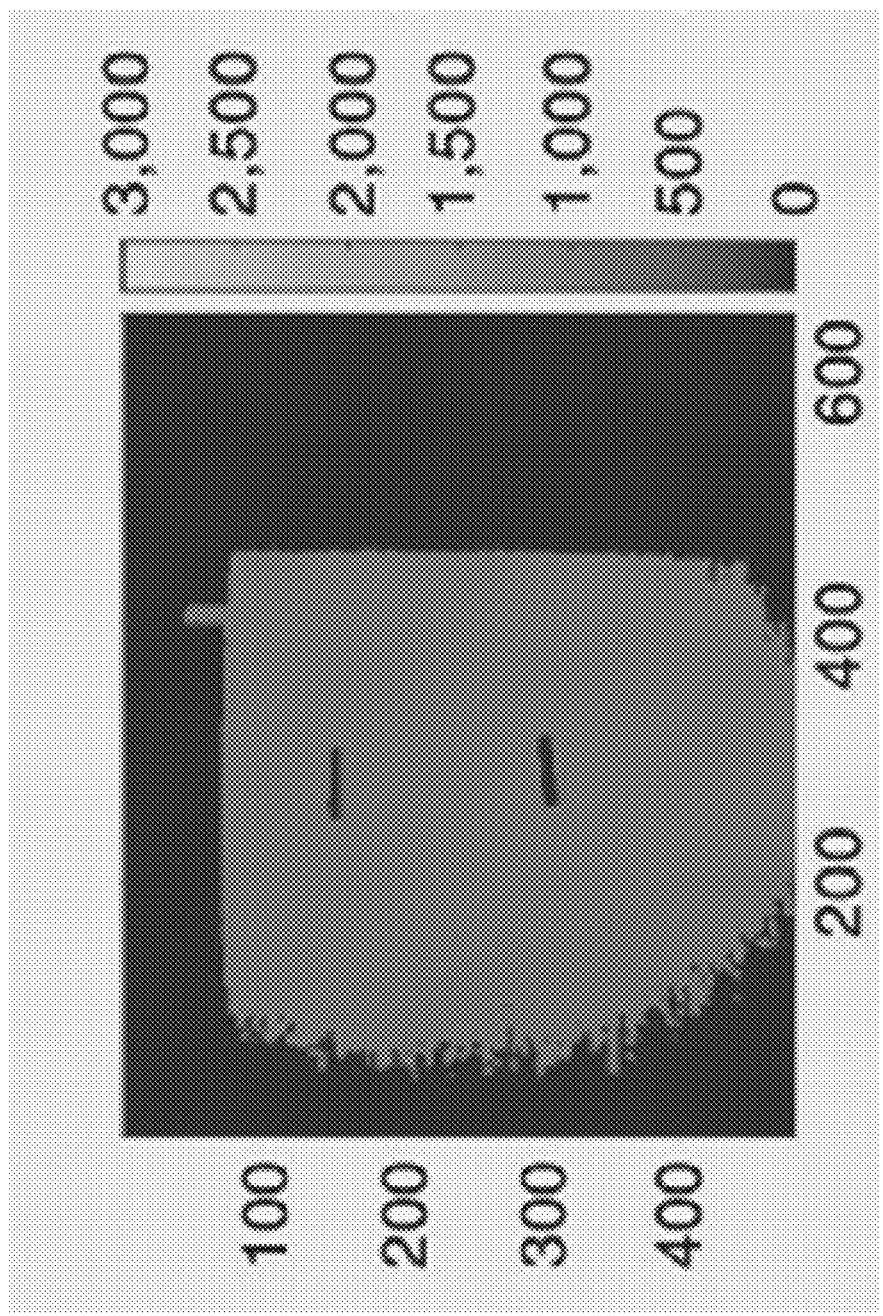
FIGS. 14A, 14B, and 14C illustrate graphs of the influence of additional sensors according to embodiments of the present disclosure.
Figure 14B:
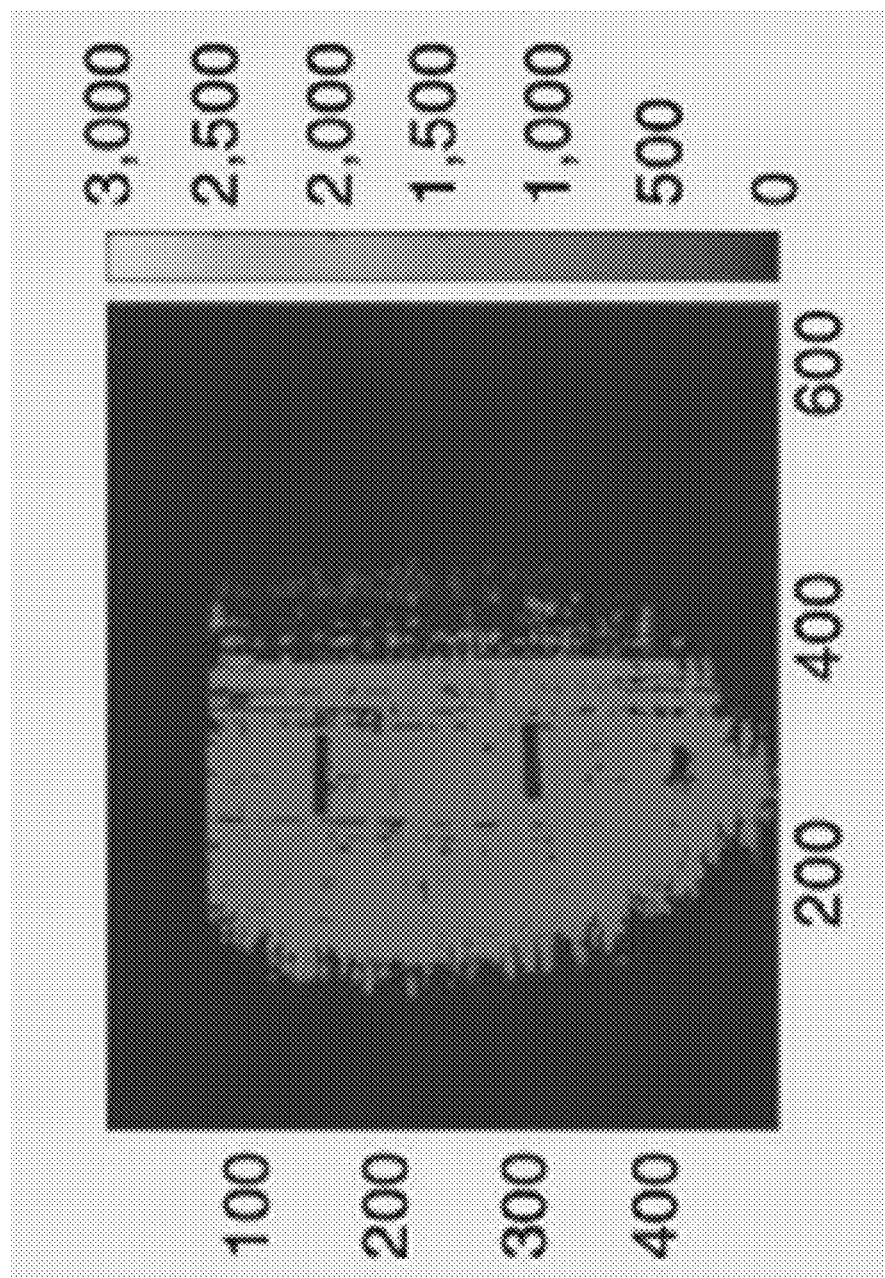
Figure 14C:
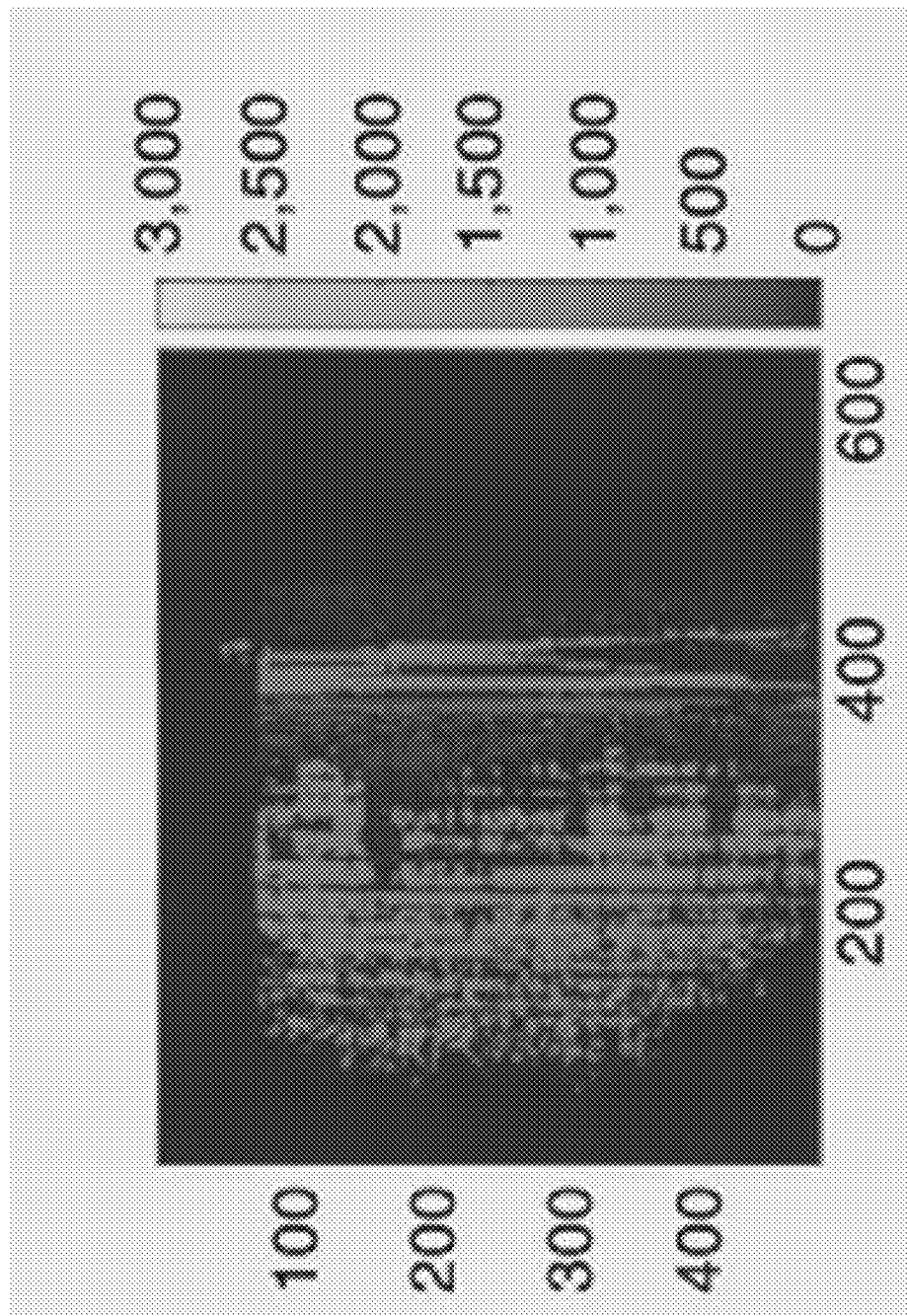

As for noise induced by additional sensors (FIGS. 13A, 13B, 14A, 14B, and 14C), the results (FIGS. 13A and 13B) reveal that the far-range structured light sensors can handle noise induced by one and two additional sensors. An exception occurs when the distance to the target is d=1.5 m and two additional sensors are introduced to the scene. A similar effect was not observed for the Kinectv2. The sensor may give stable results for precision independent of one or two additional sensors. The near-range sensors F200 and SR300 may be less precise with an additional sensor, and the Ensenso N35 is only slightly affected by a third observing sensor. At this point, we note that the high nan ratio for the close-range devices can be partially derived from our setup. Half of the scene is out of the sensor's range (FIGS. 14A, 14B, and 14C). To summarize, the first experiment with one sensor provides a baseline for the measurements with two and three sensors observing the scene. The first differences may be visible if only one sensor is added. In particular, the SR300 and F200 sensors may have a significant increase in the nan ratio if another Realsense device is added to the scene. For a closer analysis, the corresponding depth images are shown. In FIGS. 14A, 14B, and 14C, it is clear that the depth extraction is heavily influenced by an additional sensor. The Ensenso and Kinectv2 sensors may be unaffected by the additional sensors.

In various embodiments, as described above, depth data received from one or more cameras may be higher quality (e.g., more reliable) than depth data from other cameras in the imaging system. In various embodiments, the quality of the depth data may be dependent on supporting features that are external to the imaging system. For example, depth data may be higher quality and therefore given a higher weight when a camera (e.g., infrared camera) can clearly read a predetermined number of fiducial markers on a tissue. In various embodiments, if the camera cannot read the predetermined number of markers, the depth data may be of a lower quality and therefore depth data from the camera may be given a lower weight. In a similar example, when a camera can clearly read a structured light pattern from a structured light projector, the depth data resulting from the structured light may be a higher quality and therefore given a higher weight.

In various embodiments, the weights associated with each imaging system may be dependent on the confidence of the depth and/or the quality of each pixel. In various embodiments, because some imaging systems have one or more "sweet-spot" in an image with higher quality image data and one or more "dead-zone" with lower quality image data, each of the weights associated with the imaging system(s) may be parameterized at the pixel-level of an image. In various embodiments, one or more (e.g., all) of the weights may be a function of 2-dimensional points (x, y) representing pixels in an image. In various embodiments, pixels in an image may be assigned coordinate points in any suitable way as is known in the art. For example, the bottom left corner of an image may be assigned a coordinate of (0, 0) and the top right corner of the image may be assigned the maximum number of pixels in each respective axis (max x pixels, max y pixels). In an example, one imaging system (e.g., stereoscopic camera) may have high-quality image data in the center of an image and low-quality image data on the periphery. In this particular example, a higher weight may be assigned to pixels in the center of the image and the weight may decrease as the pixels move radially away from the center of the image. In various embodiments, the parametric function may be a continuous function. In various embodiments, the parametric function may be a discontinuous function (e.g., piece-wise function). In various embodiments, the parametric function may include a linear function. In various embodiments, the parametric function may include an exponential function.

In various embodiments, when an imaging system cannot compute a depth at a particular pixel, that particular pixel may be assigned a weight of zero for the particular imaging system (i.e., the particular imaging system will not contribute to the determination of depth at that particular pixel).

In various embodiments, the imaging system may include stereoscopic depth sensing. In various embodiments, stereoscopic depth sensing may work best when there are one or more uniquely identifiable features in an image (or video frame). In various embodiments, stereoscopic depth sensing may be performed using two cameras (e.g., digital cameras). In various embodiments, the cameras may be calibrated with one another. For example, the imaging system may be calibrated based on latency, frame rate, three-dimensional distance between the two cameras, various distances away from the imaging system, various lighting levels, marker types/shapes/colors, etc. In various embodiments, software known in the art may be used to control the two cameras and implement stereoscopic depth sensing. In various embodiments, a first image (or frame of a video) is captured at a first camera and a second image (or frame of a video) is captured at a second camera that is located at a predetermined distance away from the first camera. In various embodiments, a pixel disparity is computed between the first image (or frame of a video) and the second image (or frame of a video). In various embodiments, a depth may be determined from the pixel disparity value. In various embodiments, closer objects have a higher pixel disparity value and further objects have a lower pixel disparity value. In various embodiments, three-dimensional coordinates (x, y, z) may be computed from the determined depth and the camera calibration parameters. In various embodiments, stereoscopic depth sensing may be used with fiducial markers to determine depth.

In various embodiments, the imaging system may include active stereoscopic depth sensing. In various embodiments, a projector may project a pattern that is unique on a local scale. In various embodiments, any suitable pattern may be used and the pattern does not have to be known to the imaging system in advance. In various embodiments, the pattern may change over time. In various embodiments, active stereoscopic depth sensing with a projector may provide depth information for featureless images in unstructured environments.

In various embodiments, a static mask may be projected onto a surface of an object (e.g., a tissue) in a scene. For example, a physical pattern (e.g., wire mesh) may be positioned in front of a source of light and lenses may be used to focus the light pattern onto the surface.

In various embodiments, a digital micromirror (DMD) projector may be used to project a pattern on the surface of the object. In this embodiment, light shines onto an array of micromirrors (e.g., 1,000,000 mirrors arranged in a rectangle). The mirrors may be controlled to either allow or prevent the light from entering and illuminating the scene. Lenses may be used to focus the light pattern onto the scene. In various embodiments, the DMD projector may allow for programmable patterns (e.g., QR code, letter, circle, square, etc.). It will be appreciated that a similar effect may be obtained using optical metasurfaces in place of a DMD.

In various embodiments, a scanned laser projector may be used to project a pattern on the surface of the object. In this embodiments, one or more laser sources are used to project a single pixel on the surface. A high definition image may be created by shining one pixel at a time at a high frequency. In various embodiments, focusing of a pattern may not be required with a scanned laser projector. In various embodiments, the scanned laser projector may allow for programmable patterns (e.g., QR code, letter, circle, square, etc.).

In various embodiments, custom algorithms may be developed for the stereoscopic camera to detect the known programmable pattern and to determine depth data from a surface onto which the pattern is projected. In various embodiments, the depth data is computed by determining a disparity value between a first image (or video frame) from the first camera and a second image (or video frame) from the second camera.

In various embodiments, a predetermined wavelength of light may be projected onto a surface of an object depending on the material of the surface. Different materials may have different absorption and/or reflectance properties across a continuum of wavelengths of light. In various embodiments, a wavelength is selected such that light reflects off of the outer-most surface of the object. In various embodiments, if a wavelength of light is selected that penetrates the surface of the object, the resulting image may have a washed out appearance resulting in inaccurate depth data (e.g., lower accuracy, high spatiotemporal noise).

In various embodiments, the imaging system may include an interferometer. In various embodiments, a light source may illuminate a scene with an object and a sensor may measure the phase difference between the emitted and reflected light. In various embodiments, depth may be computed directly from the sensor measurement. In various embodiments, this approach may have low computational resource requirements, faster processing, work on featureless scenes, and/or work at various illumination levels.

In various embodiments, the resulting depth map including the computed depths at each pixel may be post-processed. Depth map post-processing refers to processing of the depth map such that it is useable for a specific application. In various embodiments, depth map post-processing may include accuracy improvement. In various embodiments, depth map post-processing may be used to speed up performance and/or for aesthetic reasons. Many specialized post-processing techniques exist that are suitable for use with the systems and methods of the present disclosure. For example, if the imaging device/sensor is run at a higher resolution than is technically necessary for the application, sub-sampling of the depth map may decrease the size of the depth map, leading to throughput improvement and shorter processing times. In various embodiments, subsampling may be biased. For example, subsampling may be biased to remove the depth pixels that lack a depth value (e.g., not capable of being calculated and/or having a value of zero). In various embodiments, spatial filtering (e.g., smoothing) can be used to decrease the noise in a single depth frame, which may include simple spatial averaging as well as non-linear edge-preserving techniques. In various embodiments, temporal filtering may be performed to decrease temporal depth noise using data from multiple frames. In various embodiments, a simple or time-biased average may be employed. In various embodiments, holes in the depth map can be filled in, for example, when the pixel shows a depth value inconsistently. In various embodiments, temporal variations in the signal (e.g., motion in the scene) may lead to blur and may require processing to decrease and/or remove the blur. In various embodiments, some applications may require a depth value present at every pixel. For such situations, when accuracy is not highly valued, post processing techniques may be used to extrapolate the depth map to every pixel. In various embodiments, the extrapolation may be performed with any suitable form of extrapolation (e.g., linear, exponential, logarithmic, etc.).

In various embodiments, the first imaging system, the second imaging system, and the third imaging system use the same one or more cameras (e.g., plenoptic cameras) connected to a computing node. The computing node may process a single recorded image to extract the fiducial markers, the structure light pattern, and the light-field data as separate components. Each of the separate components may be used to compute positional information (e.g., a depth map) of a surface of the object. Weighting factors may be applied to each of the computed positional information to compute a weighted average depth.

In various embodiments, systems can use any combination of the above-mentioned imaging modalities/systems to determine positional information about the surface of a tissue. In various embodiments, the systems may determine that a weight value in Equation 1 is zero (0). In this case, a system uses multiple imaging modalities/systems to acquire positional data, but determines at least one of those imaging modalities/systems does not provide reliable positional data and thus disregards the particular imaging modality/system(s) that does not provide reliable data when applying Equation 1.

In some embodiments, a stereoscopic camera may be used as an imaging system either by itself or in combination with any of the above-mentioned imaging systems.

The object from which positional information is obtained may be any suitable biological tissue. For example, the object may be an internal bodily tissue, such as esophageal tissue, stomach tissue, small/large intestinal tissue, and/or muscular tissue. In other embodiments, the object may be external tissue, such as dermal tissue on the abdomen, back, arm, leg, or any other external body part. Moreover, the object may be a bone, internal organ, or other internal bodily structure. The systems and method of the present disclosure would similarly work for animals in veterinary applications.

In various embodiments, the systems and methods described herein may be used in any suitable application, such as, for example, diagnostic applications and/or surgical applications. As an example of a diagnostic application, the systems and methods described herein may be used in colonoscopy to image a polyp in the gastrointestinal tract and determine dimensions of the polyp. Information such as the dimensions of the polyp may be used by healthcare professionals to determine a treatment plan for a patient (e.g., surgery, chemotherapy, further testing, etc.). In another example, the systems and methods described herein may be used to measure the size of an incision or hole when extracting a part of or whole internal organ. As an example of a surgical application, the systems and methods described herein may be used in handheld surgical applications, such as, for example, handheld laparoscopic surgery, handheld endoscopic procedures, and/or any other suitable surgical applications where imaging and depth sensing may be necessary. In various embodiments, the systems and methods described herein may be used to compute the depth of a surgical field, including tissue, organs, thread, and/or any instruments. In various embodiments, the systems and methods described herein may be capable of making measurements in absolute units (e.g., millimeters).

Various embodiments may be adapted for use in gastrointestinal (GI) catheters, such as an endoscope. In particular, the endoscope may include an atomized sprayer, an IR source, a camera system and optics, a robotic arm, and an image processor.

In various embodiments, a contrast agent may be applied to the surface of the object, such as the surface of a biological tissue, to provide contrast to the surface of which three-dimensional positional information is to be generated by a computer vision system. When using some visualization modalities where precision is directly proportional to contrast and texture (e.g., light-field imaging), the contrast agent may be utilized to provide contrast to the surface. In various embodiments, where soft tissue is being imaged, the surface may be substantially uniform in color and have very little texture. In this case, a contrast agent, such as an atomized dye that adheres to the tissue (e.g., the serous membrane), may be applied to the tissue. The dye may be fluoresced and provide an artificial contrast to greatly improve the level of precision in the light-field imaging system.

When contrast is used on the surface of the tissue, a calibration may be obtained prior to the application of the contrast agent to determine depth information.

FIG. 1 illustrates an exemplary image 100 of a surface 102 having fiducial markers 104 in which the image may be used as a baseline image. In FIG. 1, fiducial markers 104 are provided on the surface 102 in the form of liquid markers. The fiducial markers 104 are painted in a matrix format such that a computer vision system running on a computing node can recognize the fiducial markers 104 and compute a three dimensional surface from the image. The computer vision system may include one or more cameras that record images of the object and provide the images to the computing node running computer vision software.

In various embodiments, the computer vision system generates three-dimensional position information (X, Y, Z) for each of the fiducial markers 104. The computer vision system may further interpolate positional information between the fiducial markers 104 or may extrapolate to generate a three-dimensional model of the surface 102 of the object.

Figure 2:
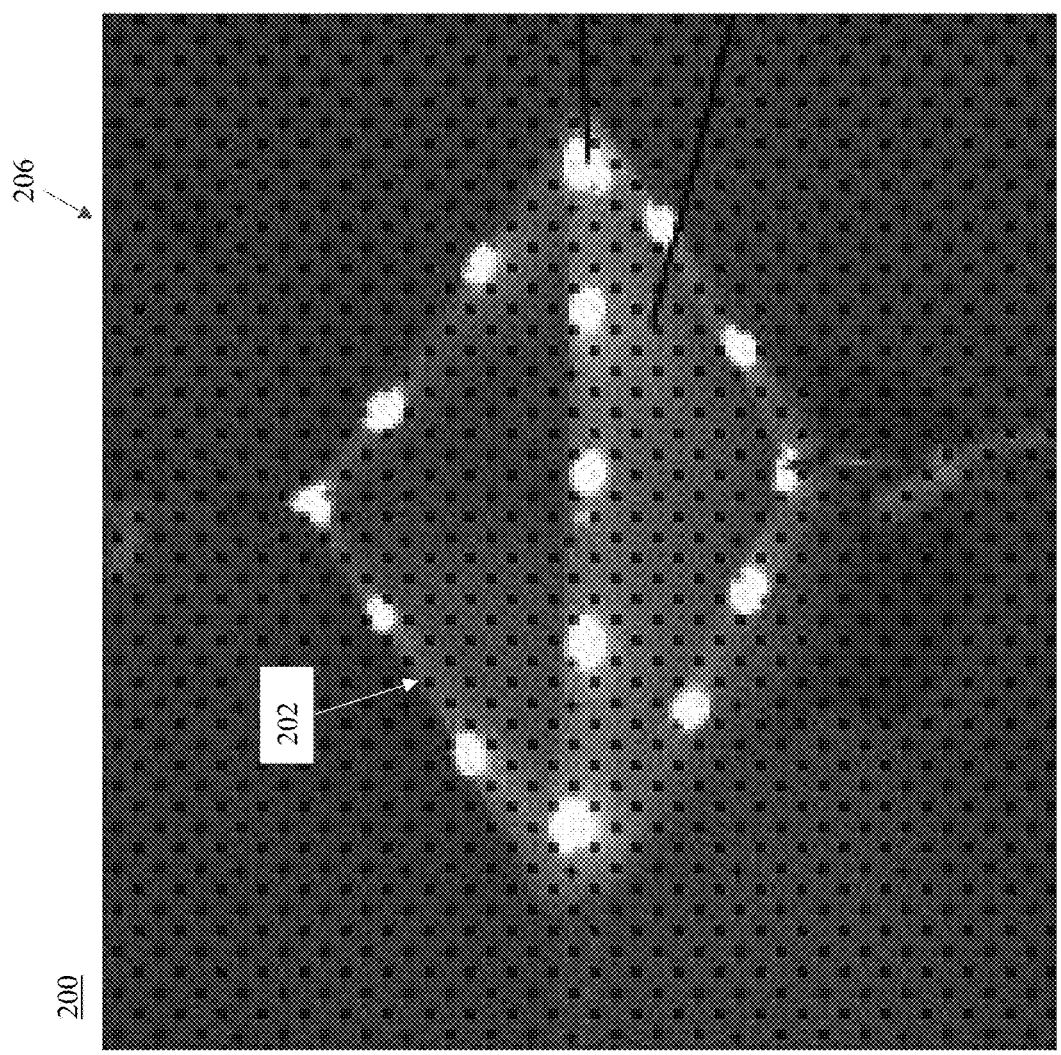
FIG. 2 illustrates an exemplary image of a surface having a matrix of structured light markers overlaying the baseline image according to embodiments of the present disclosure.

FIG. 2 illustrates an exemplary image 200 of a surface 202 having a matrix of structured light markers 206 overlaying the baseline image 100 of FIG. 1. The matrix of structured light markers 206 are in the form of a grid of dots. The structured light markers 206 are projected onto the surface 202 of the object from a source of structured light (e.g., a laser) such that a computer vision system running on a computing node can recognize the structured light markers 206 and compute a three dimensional surface from the image. The computer vision system may include one or more cameras that record images of the structured light markers 206 projected onto the object and provide the images to the computing node running computer vision software. The computer vision software may analyze the structured light markers 206 from images taken at different visual angles and perform geometric reconstruction to generate positional information of the surface 202. As shown in FIG. 2, the matrix of structured light markers 206 has more markers projected onto the surface 202 than the fiducial markers 104 shown in FIG. 1. Thus, three-dimensional positional information will be more accurate using the structured light markers 206 as there are more data points from which the computer vision software can generate the three-dimensional model of the surface 202.

Figure 3B:
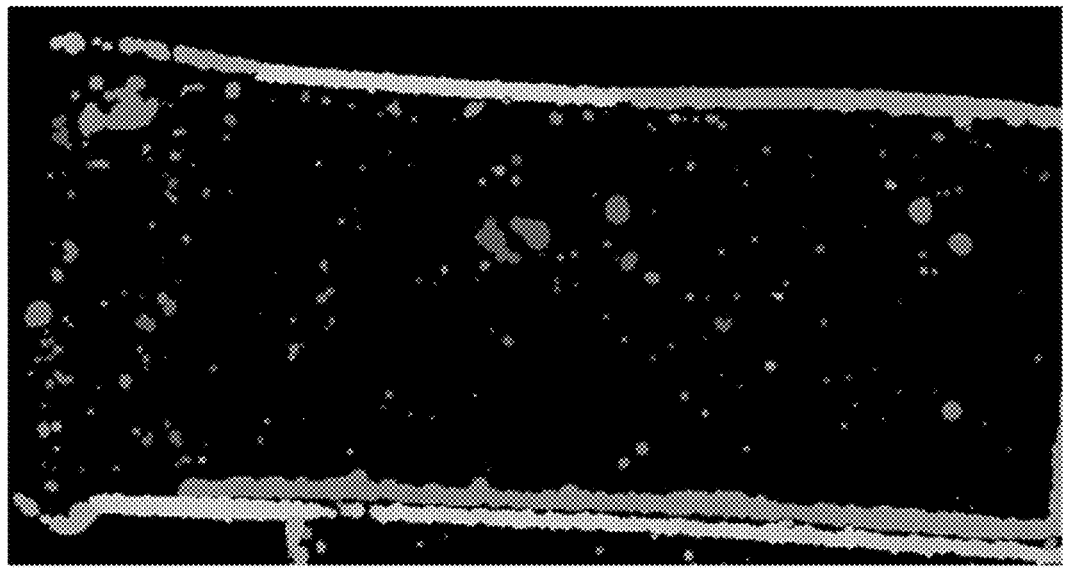
FIG. 3B illustrates an exemplary image of a depth map of simulated biological tissue according to embodiments of the present disclosure.
Figure 3A:
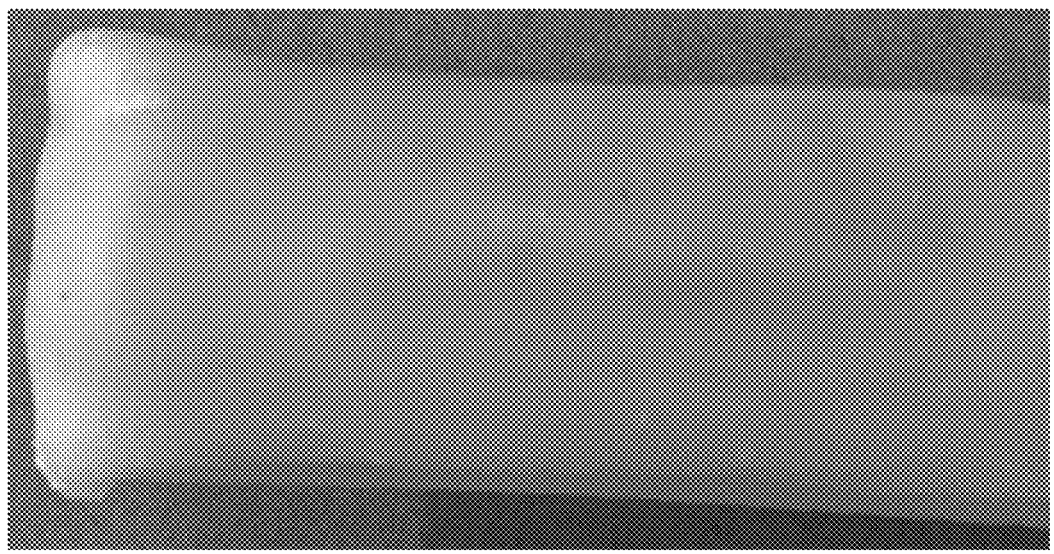
FIG. 3A illustrates an exemplary image of simulated biological tissue according to embodiments of the present disclosure.

FIG. 3A illustrates an exemplary image of simulated biological tissue 310 while FIG. 3B illustrates an exemplary image of a depth map 315 of the same simulated biological tissue 310. As shown in FIG. 3A, the simulated biological tissue 310 (e.g., a serous membrane) is substantially uniform in color, is not textured, and has no artificial markers. The depth map 315 shown in FIG. 3B represents a depth map produced by light-field imaging of the simulated tissue 310. As shown in FIG. 3B, the depth map 315 has very little to no depth data in areas of little contrast—namely, the areas of the tissue 310 away from the edges. Depth data exists at the edges because of the contrast between the simulated tissue 310 and the background.

Figure 4B:
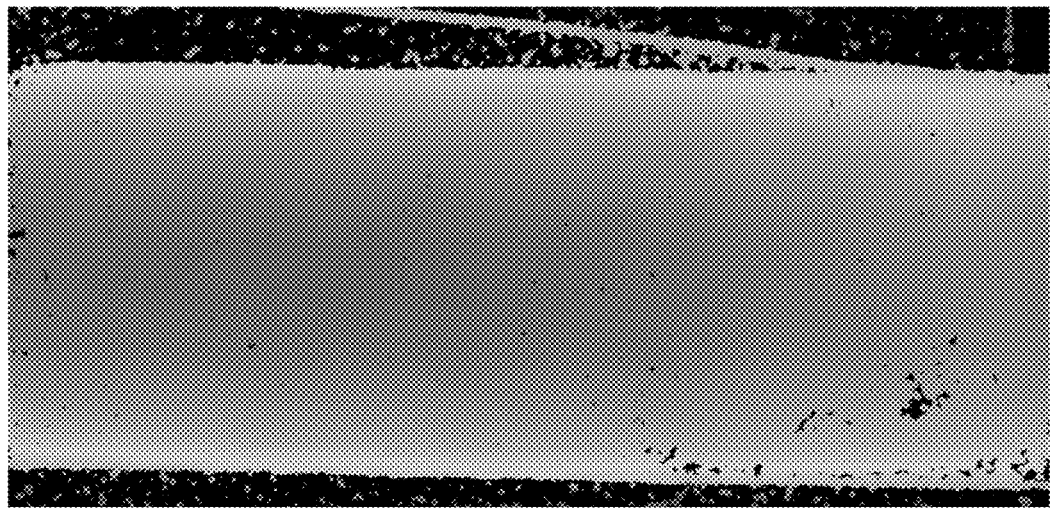
FIG. 4B illustrates an exemplary image of a depth map of simulated biological tissue having a contrast agent applied to the surface according to embodiments of the present disclosure.
Figure 4A:
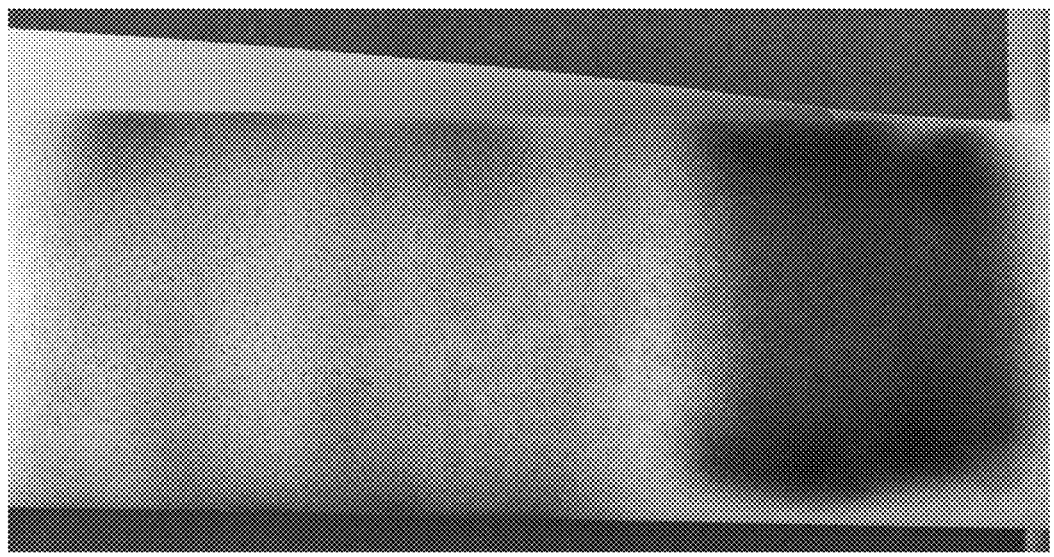
FIG. 4A illustrates an exemplary image of simulated biological tissue having a contrast agent applied to the surface according to embodiments of the present disclosure.

FIG. 4A illustrates an exemplary image of simulated biological tissue 410 having a contrast agent applied to the surface while FIG. 4B illustrates an exemplary image of a depth map 415 of the same simulated biological tissue 410 having the contrast agent. As shown in FIG. 4A, a contrast agent (e.g., an atomized blue dye) is applied to the simulated biological tissue 410 (e.g., a serous membrane). The depth map 415 shown in FIG. 4B represents a depth map produced by light-field imaging of the simulated tissue 410 having the contrast agent. As shown in FIG. 4B, the depth map 415 has much more data than the depth map 315 shown in FIG. 3B because of the contrast agent applied to the surface of the tissue. Based on the depth map 415, a computer vision system would recognize that the tissue 410 has a curved surface.

Figure 5:
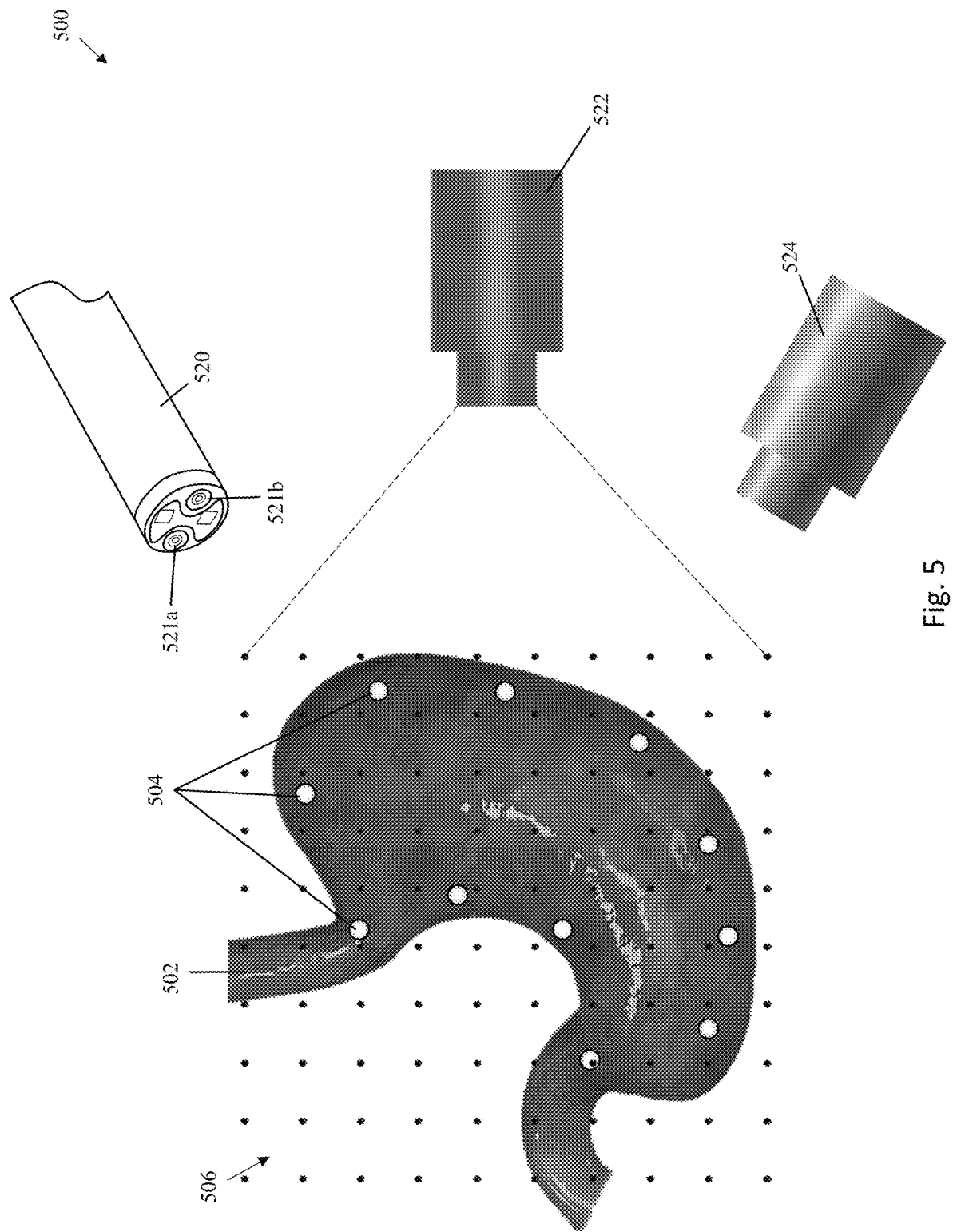
FIG. 5 illustrates a 3D surface imaging system imaging a tissue according to embodiments of the present disclosure.

FIG. 5 illustrates a 3D surface imaging system 500 imaging a tissue according to embodiments of the present disclosure. The imaging system 500 includes an endoscope 520 having cameras 521a, 521b that, when used together, generate stereoscopic images of a tissue 502 (e.g., stomach). In various embodiments, the endoscope 520 may optionally, or additionally, include an infrared camera. The tissue 502 has fiducial markers 504 disposed thereon such that a camera (e.g., infrared camera) can detect the markers 504 against the background of the tissue 502. In various embodiments, the imaging system 500 further includes a projector 522. In various embodiments, the projector 522 may be configured to project structured light 506 (e.g., a dot pattern) onto the tissue 502. In various embodiments, the projector is configured to project infrared light. The imaging system 500 further includes a light-field (e.g., plenoptic) camera 524. In various embodiments, the tissue 502 may be sprayed with a contrast liquid as described above to allow the imaging system 500 to determine depth of the tissue 502.

Figure 6:
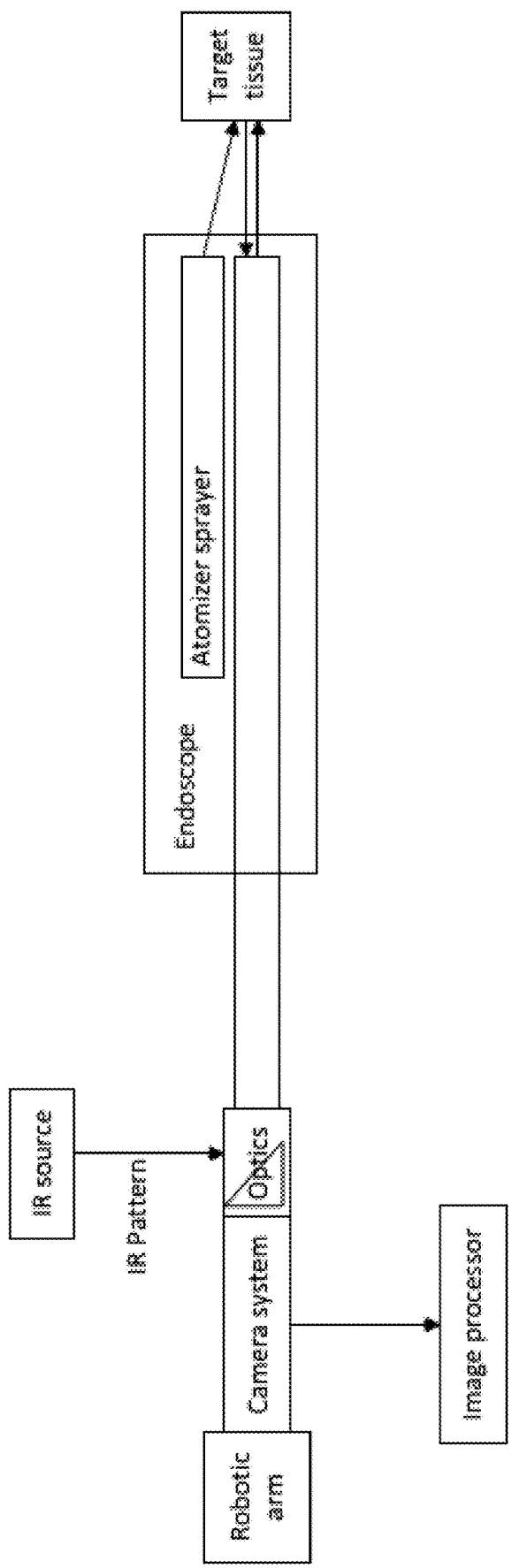
FIG. 6 shows a diagram illustrating a 3D surface imaging system according to embodiments of the present disclosure.

FIG. 6 shows a diagram illustrating a 3D surface imaging system. The system combines three visualization modalities to improve the 3D imaging resolution. The system includes a camera system that can be moved by a robotic arm. For each of the visualization modalities, the camera system captures images of target tissue through a light guide in an endoscope and an optics mechanism. The images are processed by an image processor to determine a virtually constructed 3D surface.

In one visualization modality, the camera system includes a light-field (e.g, plenoptic) camera for capturing a plenoptic image of the target tissue. The image processor uses standard techniques to determine 3D surface variation and shape from the plenoptic image.

In a second visualization modality, the system uses an IR (infrared) source/projector for generating an IR spot pattern, which is projected on the target tissue via the optics mechanism and a light guide in the endoscope. The spot pattern can be predefined or random. The camera system includes an IR sensor that captures an image of the IR spots on the target tissue. The image is transmitted to the image processor, which detects distortions in the spot pattern projected on the target tissue to determine 3D surface variation and shape.

In a third visualization modality, the system uses an atomizer/sprayer in the endoscope to apply an atomized liquid dye to selected areas of the target tissue to increase the number of fiducial spots. The atomized dye adheres to the target tissue in a random spot pattern with a higher spot concentration than the IR spot pattern. The dye can be fluoresced to provide an augmented contrast with the tissue to improve precision of the imaging system.

The image processor determines which visualization modality data is most appropriate in a given situation, and combines the data where appropriate to further improve the 3D imaging resolution. The data can be combined using a weighting algorithm. The system thereby accurately and reliably senses depth with a high resolution, which is needed for accurate robotic surgical planning and execution.

Figure 7:
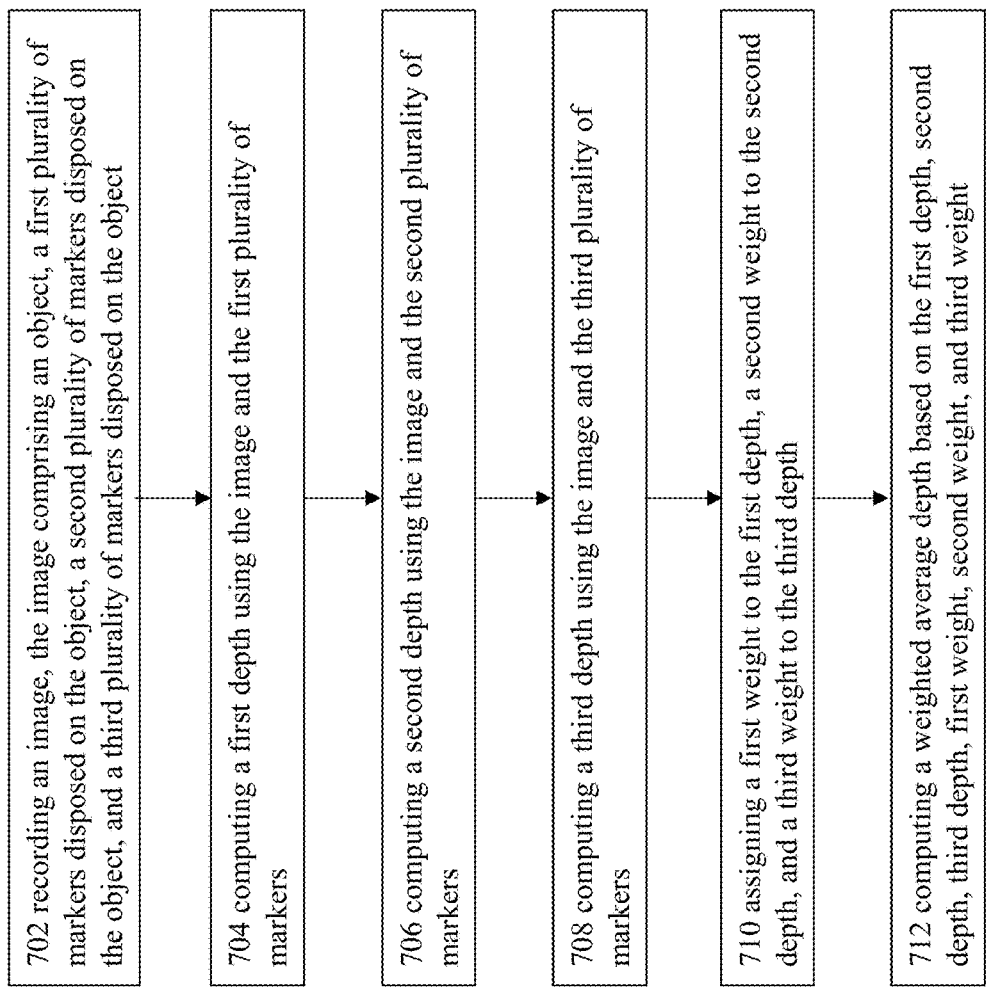
FIG. 7 shows an exemplary flowchart of a method for determining a three-dimensional coordinate on an object according to embodiments of the present disclosure.

FIG. 7 shows a flowchart 700 of a method for determining a three-dimensional coordinate on an object. At 702, the method includes recording an image, the image comprising an object, a first plurality of markers disposed on the object, a second plurality of markers disposed on the object, and a third plurality of markers disposed on the object. At 704, the method includes computing a first depth using the image and the first plurality of markers. At 706, the method includes computing a second depth using the image and the second plurality of markers. At 708, the method includes computing a third depth using the image and the third plurality of markers. At 710, the method includes assigning a first weight to the first depth, a second weight to the second depth, and a third weight to the third depth. At 712, the method includes computing a weighted average depth based on the first depth, second depth, third depth, first weight, second weight, and third weight.

Figure 15:
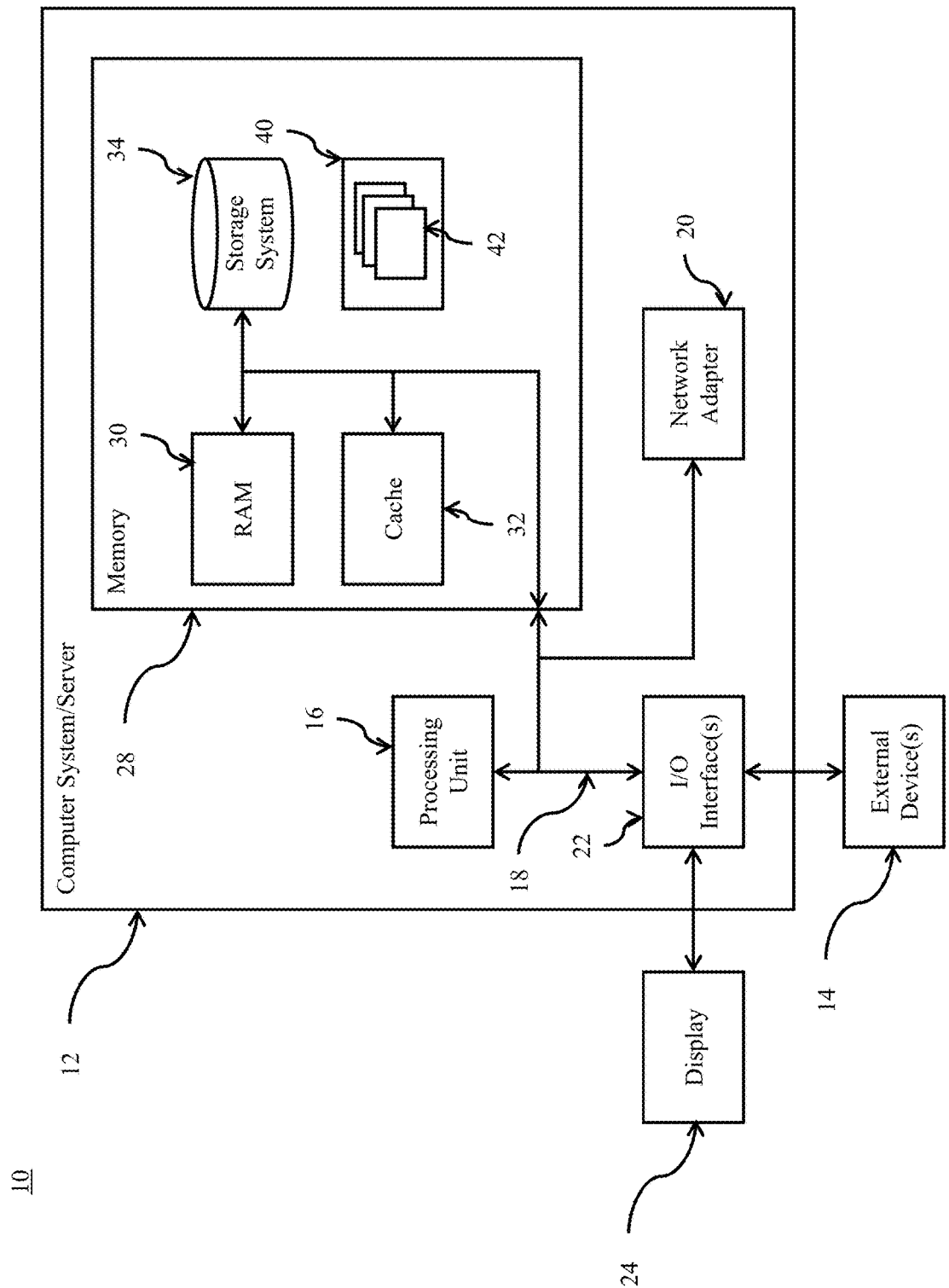
FIG. 15 shows a schematic of an exemplary computing node according to embodiments of the present disclosure.

Referring now to FIG. 15, a schematic of an exemplary computing node is shown that may be used with the computer vision systems described herein. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 15, computer system/server 12 in computing node 10 is shown in the form of a general-purpose computing device. The components of computer system/server 12 may include, but are not limited to, one or more processors or processing units 16, a system memory 28, and a bus 18 coupling various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

In other embodiments, the computer system/server may be connected to one or more cameras (e.g., digital cameras, light-field cameras) or other imaging/sensing devices (e.g., infrared cameras or sensors).

The present disclosure includes a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In various embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In various alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system for depth sensing, the system comprising:
one or more imaging devices configured to obtain a plurality of images of an object in a surgical scene using a plurality of different imaging modalities, wherein the plurality of images comprises a plurality of markers on or near the object, and wherein the plurality of imaging modalities comprises at least two of: RGB imaging, infrared imaging, depth imaging, fiducial marker imaging, structured light pattern imaging, or light field imaging; and
a processor configured to:
  (a) compute a plurality of depth measurements for at least a portion of the object based on the plurality of images; and
  (b) determine positional information for at least the portion of the object based on the plurality of depth measurements, wherein one or more weights are assigned to the plurality of depth measurements, wherein each of the one or more weights has a value between zero (0) and one (1), wherein a sum of the one or more weight values assigned to the plurality of depth measurements equals one (1), and wherein the plurality of depth measurements are weighted based at least in part on a type of imaging modality used to obtain one or more images of the plurality of images.

2. The system of claim 1, wherein the positional information comprises (i) a three-dimensional position of at least the portion of the object or (ii) one or more three-dimensional coordinates for at least the portion of the object.

3. The system of claim 1, wherein the plurality of depth measurements are weighted based at least in part on (i) a quality or a property of the one or more images or (ii) a reliability, an accuracy, or a precision of one or more depth measurements of the plurality of depth measurements.

4. The system of claim 1, wherein the plurality of depth measurements are weighted based at least in part an imaging performance, an imaging condition, or an imaging parameter of the one or more imaging devices.

5. The system of claim 1, wherein the one or more weights are parameterized at a pixel-level for the one or more images.

6. The system of claim 1, wherein the plurality of markers comprises different types of markers that are detectable using different imaging modalities.

7. The system of claim 1, wherein the plurality of images comprises (i) a baseline image comprising at least a subset of the plurality of markers and (ii) an additional image comprising a different subset of the plurality of markers.

8. The system of claim 1, wherein the plurality of markers comprises one or more fiducials that are physically applied to the object or the surgical scene.

9. The system of claim 8, wherein the one or more fiducials comprise a symbol, a pattern, a shape, a marker, a liquid, an ink, or a dye.

10. The system of claim 1, wherein the plurality of markers comprises one or more fiducials that are projected onto the object or the surgical scene, wherein the one or more fiducials comprise one or more structured light markers or optical markers.

11. The system of claim 10, further comprising a light source configured to project a pattern onto a surface of the object, wherein the pattern comprises or corresponds to the one or more structured light markers or optical markers.

12. The system of claim 11, wherein the processor is configured to (i) detect one or more changes in a size, a shape, or a configuration of the pattern when the pattern is projected on the surface of the object and (ii) determine the positional information for the object based on the one or more detected changes.

13. The system of claim 11, wherein the processor is configured to geometrically reconstruct a portion of the surface of the object based on a comparison between (i) the pattern projected onto the surface of the object and (ii) a known or predetermined pattern.

14. The system of claim 1, wherein the processor is configured to generate a depth map or a three-dimensional map of a surface of the object based on the positional information.

15. The system of claim 14, wherein the processor is configured to post-process the depth map or the three-dimensional map of the surface of the object by implementing one or more subsampling, spatial filtering, temporal filtering, blur removal, time-biased averaging, or extrapolation operations or techniques.

16. The system of claim 1, wherein the processor is configured to determine or measure one or more dimensions of the object based on the positional information.

17. The system of claim 1, further comprising an interferometer configured to measure a phase difference between (i) light emitted or transmitted to the surgical scene and (ii) light reflected from the surgical scene to obtain one or more additional depth measurements usable to determine or update the positional information.

18. The system of claim 1, wherein the one or more imaging devices comprise an RGB camera, an infrared camera, a stereoscopic camera, a light-field camera, a plenoptic camera, or a structured light detection unit.

19. The system of claim 1, wherein the object comprises a biological material, a tissue, an organ, an internal bodily structure, or an external bodily structure.

20. A system for depth sensing, the system comprising:
one or more imaging devices configured to obtain a plurality of images of an object in a surgical scene using a plurality of different imaging modalities, wherein the plurality of images comprises a plurality of markers on or near the object, and wherein the plurality of imaging modalities comprises at least of: RGB imaging, infrared imaging, depth imaging, fiducial marker imaging, structured light pattern imaging, or light field imaging; and
a processor configured to:
  (a) compute a plurality of depth measurements for at least a portion of the object based on the plurality of images; and
  (b) determine positional information for at least the portion of the object based on the plurality of depth measurements, wherein one or more weights are assigned to the plurality of depth measurements, wherein the one or more normalized weights have values between a predefined range, and wherein the plurality of depth measurements are weighted based on a type of imaging modality used to obtain one or more images of the plurality of images.

21. A system for depth sensing, the system comprising:

one or more imaging devices configured to obtain a plurality of images of an object in a surgical scene using a plurality of different imaging modalities, wherein the plurality of images comprises a plurality of markers on or near the object, and wherein the plurality of imaging modalities comprises at least two of: RGB imaging, infrared imaging, depth imaging, fiducial marker imaging, structured light pattern imaging, or light field imaging; and a processor configured to:
  (a) compute a plurality of depth measurements for at least a portion of the object based on the plurality of images; and
  (b) determine positional information for at least the portion of the object based on the plurality of depth measurements, wherein one or more weights are assigned to the plurality of depth measurements, wherein each of the one or more weights has a value between a first value and a second value that is greater than the first value, wherein a sum of the one or more weight values assigned to the plurality of depth measurements sums to unity, and wherein the plurality of depth measurements are weighted based at least in part on a type of imaging modality used to obtain one or more images of the plurality of images.

* * * * *